(12) United States Patent
Roderique

(10) Patent No.: US 10,314,857 B2
(45) Date of Patent: Jun. 11, 2019

(54) COMPOSITIONS AND METHODS FOR TREATING CARBON MONOXIDE AND/OR CYANIDE POISONING

(71) Applicant: Virginia Commonwealth University, Richmond, VA (US)

(72) Inventor: Joseph D. Roderique, Richmond, VA (US)

(73) Assignee: VIRGINIA COMMONWEALTH UNIVERSITY, Richmond, VA (US)

( * ) Notice: Subject to any disclaimer, the term of this patent is extended or adjusted under 35 U.S.C. 154(b) by 0 days.

(21) Appl. No.: 14/790,568

(22) Filed: Jul. 2, 2015

(65) Prior Publication Data

US 2016/0000820 A1    Jan. 7, 2016

Related U.S. Application Data

(60) Provisional application No. 62/020,185, filed on Jul. 2, 2014.

(51) Int. Cl.
| | | |
|---|---|---|
| *A61K 31/714* | (2006.01) | |
| *A61K 9/00* | (2006.01) | |
| *A61K 47/22* | (2006.01) | |
| *A61J 1/05* | (2006.01) | |
| *A61J 1/20* | (2006.01) | |

(52) U.S. Cl.
CPC .......... *A61K 31/714* (2013.01); *A61K 9/0019* (2013.01); *A61K 47/22* (2013.01); *A61J 1/05* (2013.01); *A61J 1/2093* (2013.01)

(58) Field of Classification Search
CPC .................................................. A61K 31/714
See application file for complete search history.

(56) References Cited

U.S. PATENT DOCUMENTS

2006/0188607 A1 * 8/2006 Schramm ............... A23D 7/005
                                                                    426/72
2011/0293759 A1 * 12/2011 Westerlund .......... A61K 31/122
                                                                    424/777

FOREIGN PATENT DOCUMENTS

WO       WO 0224165 A2 *  3/2002   ........... A61K 9/0095

OTHER PUBLICATIONS

Dolphin, D., Preparation of the Reduced Forms of Vitamin B12 and of Some Analogs of the Vitamin B12 Coenzyme Containing a Cobalt-Carbon Bond, 1971, Vitamins and Coenzymes, vol. XVIII, Part C, pp. 34-54 (Year: 1971).*
Ahmad et al., Effect of Ascorbic Acid on the Degradation of Cyanocobalamin and Hydroxocobalamin in Aqueous Solution: A Kinetic Study, 2014, AAPS PharmSciTech, vol. 15, No. 5, pp. 1324-1333 (Year: 2014).*
Gaby, A., Intravenous Nutrient Therapy: the "Myers' Cocktail", 2002, Alternative Medicine Review, vol. 7, No. 5, pp. 389-403 (Year: 2002).*
Alden Newcomb, "Evaluation of the Physiological Effects of Reduced Hydroxocobalamin on Acute Carbon Monoxide Toxicity", Thesis (Jul. 2014).
Joseph Roderique, "Studies on the Reaction of High-Dose Hydroxocobalamin and Ascorbic Acid With Carbon Monoxide: Implications for Treatment of Carbon Monoxide Poisoning", Thesis (Mar. 2013).
Leonardo Somera, "Hydroxocobalamin Treatment for Carbon Monoxide Exposures: Characterizing Hemoglobin Changes and Testing for Neurological Sequelae", Thesis (Feb. 2014).
Manzanares et al, "Vitamin B12: the forgotten micronutrient for critical care", Curr OpinClin Nutr Metab Care 13, 662-668 (2010).
Wheatley, "A scarlet pimpernel for the resolution of inflammation? The role of supra-therapeutic doses of cobalamin, in the treatment of systemic inflammatory response syndrome (SIRS), sepsis, severe sepsis, and septic or traumatic shock", Medical Hypotheses 67, 124-142 (2006).
Sharma et al, "Reactions of nitric oxide with vitamin B12 and its precursor, cobinamide", Biochemistry 42, 8900-8908 (2003).
Davidge et al., "Carbon Monoxide in Biology and Microbiology: Surprising Roles for the 'Detroit Perfume'", Advances in Microbial Physiology, vol. 56, 85-167 (Academic Press, 2009).
Cui et al, "Factors contributing to one-electron metalloradical activation of ethene and carbon monoxide illustrated by reactions of Co(II), Rh(II), and Ir(II) porphyrins", Journal of Organometallic Chemistry 692, 3198-3206 (2007).

* cited by examiner

*Primary Examiner* — Jeffrey S Lundgren
*Assistant Examiner* — Tori Strong
(74) *Attorney, Agent, or Firm* — W&C IP

(57) ABSTRACT

Compositions, methods and kits for treating victims of carbon monoxide and/or cyanide poisoning and/or nitric acid-induced vasoplagia are provided. The compositions comprise reduced forms of Vitamin B12 such as reduced hydroxocobalamin or reduced cobinamide, and typically comprise at least one reducing agent (e.g. ascorbic acid). The compositions are generally produced, stored and delivered under reducing, usually anaerobic, conditions in order to preserve the desired oxidation state when introduced into the blood stream of a recipient.

9 Claims, 20 Drawing Sheets

A.
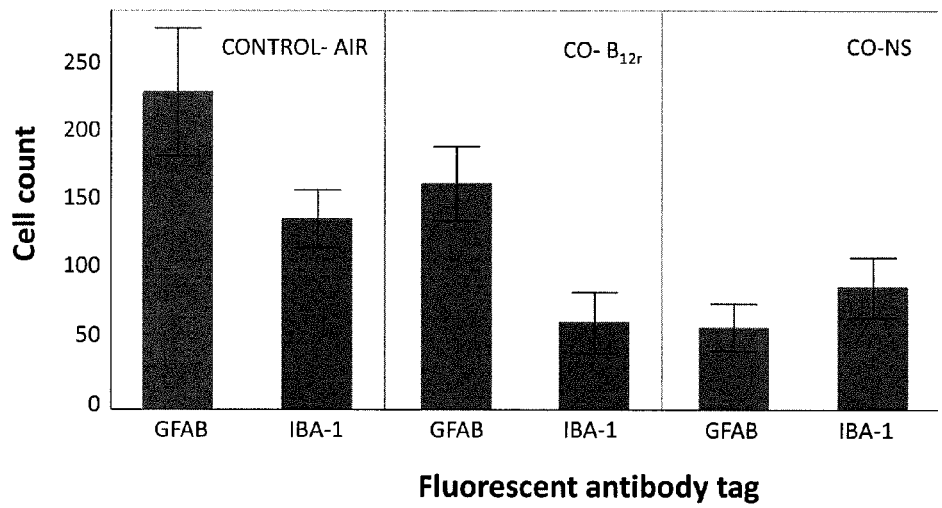
B.
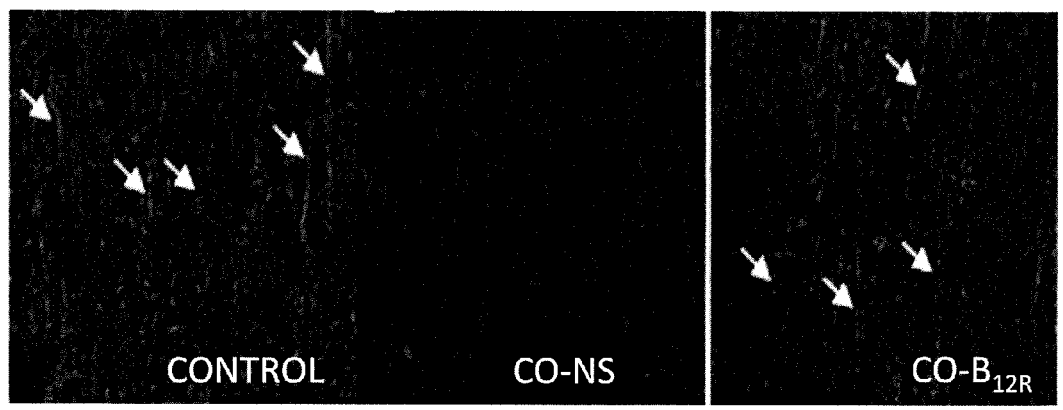
Figure 5A and B

C.

A.
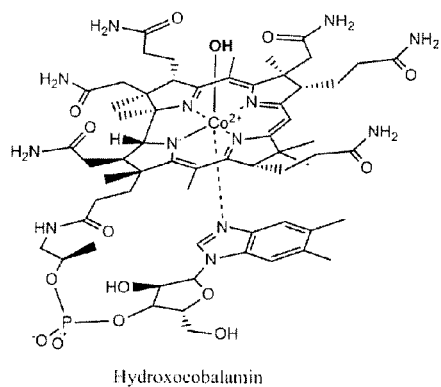
Hydroxocobalamin
B.
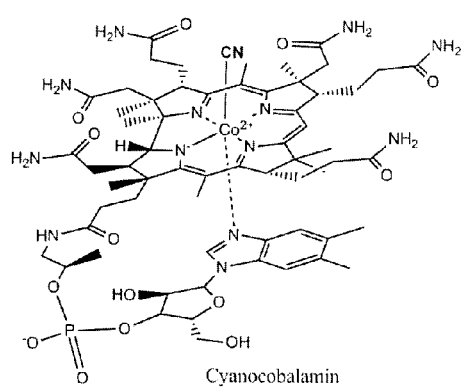
Cyanocobalamin
C.
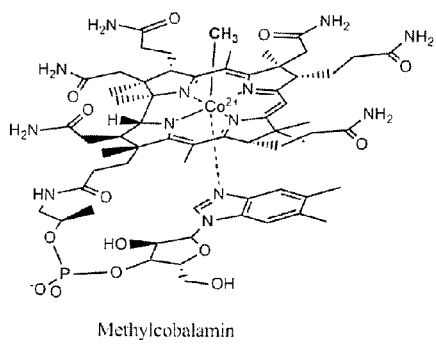
Methylcobalamin
D.
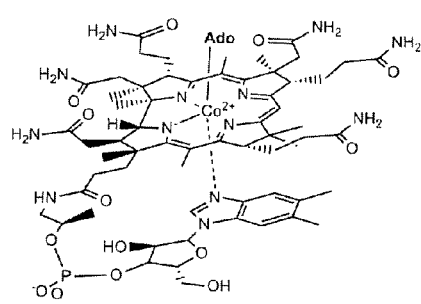
Adenosylcobalamin
Figure 6 A-D

E.

A.
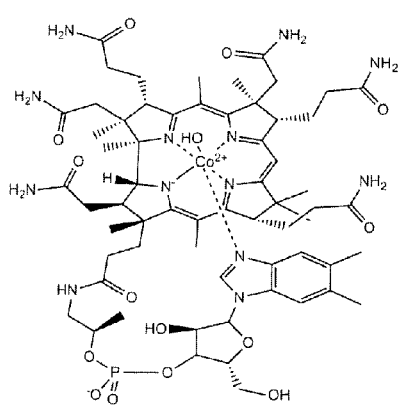
Base-On
B.
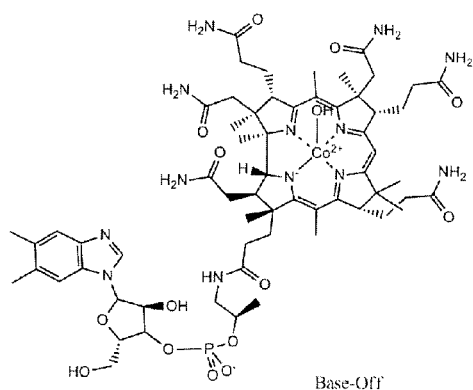
Base-Off
C.
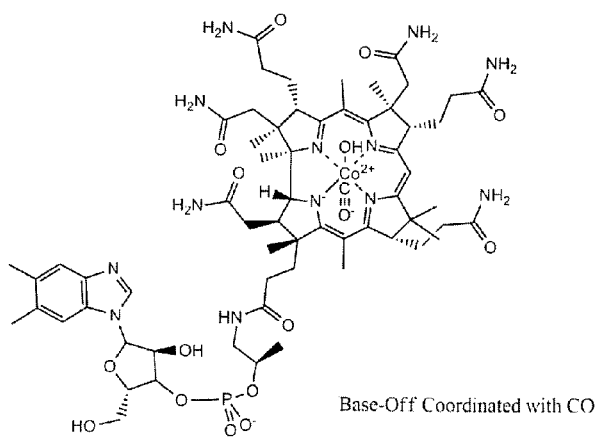
Base-Off Coordinated with CO
Figure 7 A-C

COMPOSITIONS AND METHODS FOR TREATING CARBON MONOXIDE AND/OR CYANIDE POISONING

BACKGROUND OF THE INVENTION

Field of the Invention

The invention generally relates to compositions and methods for treating victims of carbon monoxide and/or cyanide poisoning. In particular, the compositions comprise reduced forms of Vitamin B12 such as hydroxocobalamin or cobinamide to treat victims of carbon monoxide and/or cyanide poisoning (such as victims of smoke inhalation).

Background of the Invention

Carbon monoxide (CO) exposure is the leading cause of unintentional poisoning death and long-term morbidity in the US. In 2012 alone, there were over 13,000 cases reported to US poison centers, with 143 serious outcomes and 54 deaths[1]. However serious delayed sequelae such as persistent and recurrent neurological deficits may occur in up to 30% of patients following apparent recovery from acute symptoms; these delayed neurological complications (DNS) may not become evident until weeks or months after exposure[2]. Reduction in $O_2$ delivery to the tissues is thought to result from binding of CO to hemoglobin (Hgb) to form carboxyhemoglobin (COHgb). Carbon monoxide binds with Hgb with an affinity that is 200-250 times greater than oxygen, thus rendering the concentration of oxyhemoglobin lower in patients with CO exposure. In addition the binding of carbon monoxide to Hgb results in conformational changes in Hgb that reduces its ability to offload its remaining $O_2$ to the tissues and subsequently causing hypoxic injury. As a result, current acute-care management involves either normobaric (NBO) or hyperbaric (HBO) oxygen therapy; however, the efficacy of oxygen therapy for prevention of DNS specifically is uncertain and has not been evaluated systematically[3]. Further limitations of oxygen therapy include unpredictable availability of equipment and delays between point of exposure, recognition of signs and symptoms, and initiation of therapy[4]. No antidotes for CO toxicity currently exist.

Victims of smoke inhalation typically suffer from exposure to both CO and cyanide (polyintoxication). While hydroxocobalamin has been used to treat cyanide poisoning and smoke inhalation for over 40 years, the form that has been used to date is effective in scavenging only cyanide; CO exposure must be treated using $O_2$ as described above.

To be clinically useful, proposed antidotes for CO toxicity must be readily available, field-deployable, targeted, rapidly effective, and safe. Thus, what is needed are efficacious compositions and methods of treating CO poisoning, and for treating CO and cyanide poisoning together using a single formulation.

SUMMARY OF THE INVENTION

Aspects of the invention include compositions which serve as antidotes to both cyanide and carbon monoxide poisoning, in subjects in need thereof, including victims of smoke inhalation injury. The compositions comprise reduced forms or derivatives of Vitamin B12 such as hydroxocobalamin or cobinamide sulfite. The active component of these agents is the cobalt moiety at its center, which normally (e.g. in the presence of oxygen) exists in a 3+ oxidation state, and hydroxocobalamin with cobalt in this 3+ oxidation state (B12a) is FDA approved for the treatment of cyanide poisoning, but is not useful for scavenging CO. However, data presented herein shows that the reduced form of hydroxocobalamin (B12r), with the cobalt moiety in the 2+ oxidation state, allows it to react with carbon monoxide in addition to cyanide. When administered to a patient, B12r converts carbon monoxide in the blood into carbon dioxide which is readily diffused across the lungs and exhaled, thus returning hemoglobin to its normal functioning state. Kits and delivery systems which prevent the introduction of oxygen during administration are also provided. In addition, the compositions described herein are also useful for the removal of excess nitric oxide in the blood.

Other features and advantages of the present invention will be set forth in the description of invention that follows, and in part will be apparent from the description or may be learned by practice of the invention. The invention will be realized and attained by the compositions and methods particularly pointed out in the written description and claims hereof.

It is an object of this invention to provide pharmaceutical compositions comprising hydroxocobalamin and/or cobinamide, at least one reducing agent, and a pharmaceutically acceptable carrier. In some aspects, the pharmaceutical composition is de-oxygenated. In some aspects, the reducing agent is ascorbic acid. In some aspects, the hydroxocobalamin and/or cobinamide are in reduced form. In some aspects, an oxidation state of at least a portion of cobalt in said hydroxocobalamin and/or said cobinamide is 2+ or +1.

The invention also provides methods of treating carbon monoxide (CO) poisoning, said method comprising the step of administering, to a subject suffering from CO poisoning, a therapeutically effective amount of a composition comprising hydroxocobalamin and/or cobinamide, at least one reducing agent, and a pharmaceutically acceptable carrier. In some aspects, the step of administering is carried out in a manner that prevents exposure of said composition to oxygen. In some aspects, the concentration of the hydroxocobalamin and/or cobinamide in the composition is from about 5 mg/ml to about 25 mg/ml, and a concentration of the at least one reducing agent is from about 1 mg/ml to about 25 mg/ml. In aspects of the invention, the composition is administered intravenously or intramuscularly.

The invention also provides delivery systems for the administration of the compositions described herein comprising i) a first sealed compartment containing solidified hydroxocobalamin and/or cobinamide; and ii) a second sealed compartment containing a de-oxygenated pharmaceutically acceptable liquid carrier. Oxygen is generally not present in the first sealed compartment and the second sealed compartment. In some aspects, the first sealed compartment is positioned within the second sealed compartment. In other aspects, the first sealed compartment is connected (e.g. directly or indirectly) to an exterior surface of the second sealed compartment. In other aspects, the delivery system comprises a syringe, and the first sealed compartment is located adjacent to the second sealed compartment within a barrel of said syringe. In aspects of the invention, a first sealed compartment also contains at least one solidified reducing agent. In additional aspects, the first and second sealed compartments are impenetrable by UV light.

The invention also provides medicaments comprising a reduced Vitamin B12 compound in an inert environment suitable for delivery to a subject (the reduced Vitamin B12 compound being selected from reduced hydroxocobalamin and reduced cobinamide) and further comprising pharmaceutically acceptable salts. In certain aspects, the medicament further comprises one or more reducing agents, such as, for example, ascorbic acid, zinc-mercury amalgam, Lindlar catalyst, sodium borohydride, sodium dithionate, formic acid, and platinum oxide. In some aspects, the reduced Vitamin B12 compound is in solid form, which may be, for example, crystalline or amorphous. In other aspects, the reduced Vitamin B12 compound is in liquid form. In certain aspects, the inert environment comprises one or more inert gases. In other aspects, the inert environment comprises a deoxygenated liquid.

BRIEF DESCRIPTION OF THE DRAWINGS

FIG. 5A-C. Immunochemistry of brain tissue of rats exposed to medical air (CONTROL) or CO with either antidote ($B_{12r}$) or NS control solution. A. Mean (SD) microglial and astrocyte cell counts of GFAP and Iba-1 tagged cells; B Relative myelination: Myelinated axons are indicated by white arrows. Note the paucity of myelin in the CO poisoned rats (center panel); C. Microglial activation. Arrows highlight activated microglia based on increased Iba-1 staining density, thickened processes, and loss of arborization.

FIG. 5A-C. Schematic representations of exemplary delivery systems. A, internal pouch; B, external container; C, modified syringe.

FIG. 6A-E. Exemplary Vitamin B12 compounds A, hydroxocobalamin; B, cyanocobalamin; C, methylcobalamin; D, adenosylcobalamin; E, cobinamide.

FIG. 7A-C. Exemplary illustration of the intermediary steps in the coordination of CO with hydroxocobalamin. A, base-on; B, base-off; and C, base-off coordinated with CO for hydroxocobalamin.

DETAILED DESCRIPTION

Figure 1:
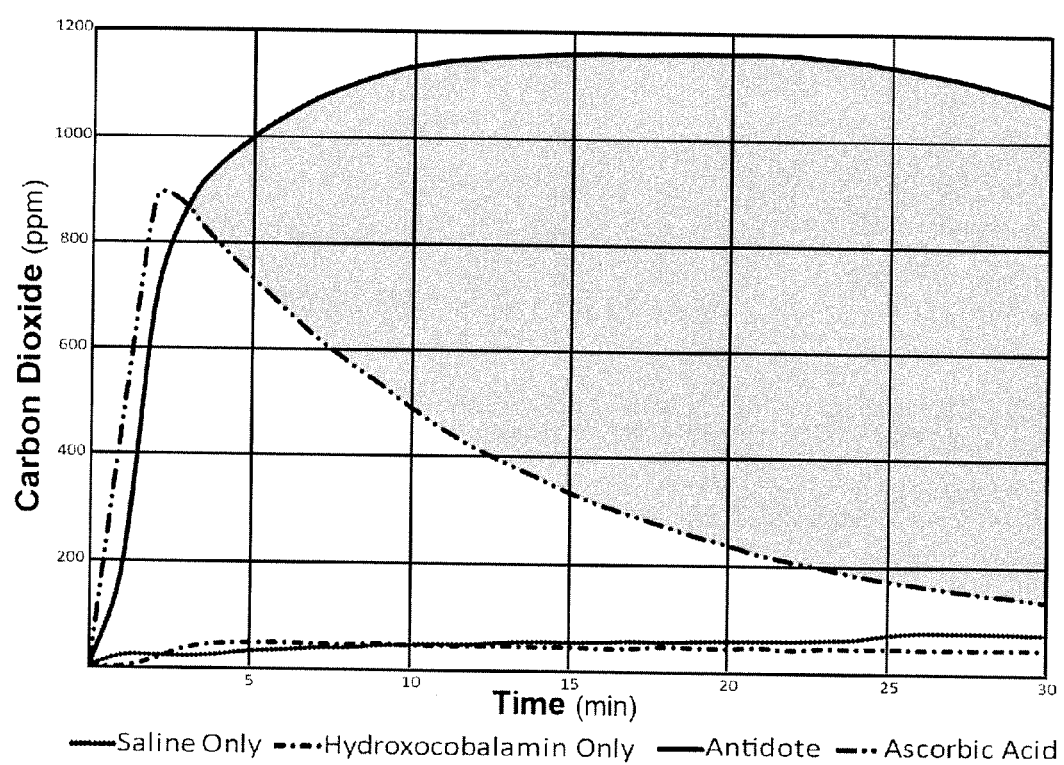
FIG. 1. Comparative $CO_2$ production (ppm/min) over 30 min induced by $B_{12r}$ antidote (hydroxocobalamin $B_{12}$+ ascorbic acid) added to whole human blood containing 50% COHgb. The shaded area is the difference between $CO_2$ produced from ascorbic acid alone, and that produced by $B_{12r}$. Little or no $CO_2$ was produced by infusion of normal saline (NS) or oxidized hydroxocobalamin.

Compositions and methods of using the compositions as antidotes to carbon monoxide and/or cyanide poisoning in subjects are described herein. The compositions comprise reduced forms or derivatives of Vitamin B12 such as reduced hydroxocobalamin and reduced cobinamide sulfite, plus at least one reducing agent. The reduced forms of these agents are extremely reactive with oxygen in the air or in solution and are produced, maintained and administered under strict anaerobic conditions. Administration of the compositions to a subject in need thereof converts carbon monoxide in the blood into carbon dioxide which is readily diffused across the lungs and exhaled, thus returning hemoglobin to its normal functioning state. Due to its reactivity, a composition comprised of cobinamide sulfite requires roughly half the active ingredient of current oxidized B12a formulations and thus can be infused in about half the volume and time (e.g. 15 minutes instead of 30 minutes). Unique delivery systems which prevent the introduction of oxygen into the system prior to and during delivery are also described. The combinations are also used to lower nitric oxide levels in the blood, for example, in patients experiencing high levels of NO in the blood in the aftermath of CO poisoning, or patients suffering from NO-induced vasoplegia as a result of open heart surgery.

The following definitions are used throughout:

By "anaerobic" we mean relating to, involving, or requiring an absence of free oxygen. A "reducing agent" reduces other substances, especially by donating an electron or electrons, and thus loses electrons. Therefore, its oxidation state increases and that of the reduced substance decreases.

Four compounds (hydroxocobalamin or "B12a", cyanocobalamin, adenosylcobalamin, and methylcobalamin) are commonly referred to collectively as "Vitamin B12". As used herein "reduced Vitamin B12" or "reduced B12 species" (variants, derivatives, etc.) refers to reduced hydroxocobalamin ("B12r") and/or reduced cobinamide, a tetrapyrrole of the corrinoid family (which also includes Vitamin B12), or any other reduced Vitamin B12 variant or derivative that is capable of scavenging CO. Exemplary Vitamin B12 compounds are depicted in FIG. 6A-E; exemplary depictions of base-on, base-off and CO coordination are depicted in FIG. 7A-C.

A "solid" or "solidified" substance refers to a substance that has a fixed shape and volume; this is a state of matter which, unlike a gas or liquid, is characterized by particles arranged such that their shape and volume are relatively stable. Solid forms include crystals, powders, flakes, particles, amorphous particles or pieces, etc. of a substance.

Compositions

The invention provides compositions (formulations) for use in the treatment of exposure to/poisoning by carbon monoxide, cyanide and/or excess nitric acid. The compositions generally comprise at least one active agent that is a reduced form or derivative (variant) of Vitamin B12, usually or optionally in combination with at least one reducing agent. In the reduced forms of Vitamin B12, cobalt is in the 2+ oxidation state, or alternatively, in the +1 state. Both +1 reduced forms of Vitamin B12 and +2 reduced forms of Vitamin B12 may be present in a composition. In one aspect, shat is provided herein are solid (e.g. crystalline, amorphous particles, etc.) forms of such reduced forms of Vitamin B12, which may be solidified or crystallized alone or with at least one reducing agent, as well as compositions for administration in which the solid forms are dissolved or dispersed in a physiologically acceptable carrier.

Reduced forms of Vitamin B12 that may be used in the practice of the invention include but are not limited to: hydroxocobalamin, cobinamide, etc.

In some embodiments, the medicament can include a mixed formulation of reduced and oxidized species, e.g. a mixture of B12 species in both 3+ (oxidized) and 2+ (reduced) oxidation states. In general, the ratio of 3+ to 2+ of a species is generally in the range of from about ⅓ to about 1/10, e.g. about ⅓, ¼, ⅕, ⅙, 1/7, ⅛, 1/9 or 1/10. Typically, the ratio is about 1/10. For example, for reduced hydroxocobalamin (B12r) the ratio to oxidized hydroxocobalamin (B12a) is generally about 10:1, i.e. the ratio may be from about 2.2:0.23, 2.1:0.23, 2.0:0.25, 1.9:0.27, 1.8:0.30, 1.7: 0.34, 1.6:0.4, or 1.5:0.5.

The reduced B12 species are generally provided as solids, e.g. in a crystalline form, for dissolution in a carrier just before administration. Methods of making reduced B12 species are known in the art and include those outlined in the Examples section below. Briefly, a species of interest is deoxygenated e.g. by being placed in a buffer or other aqueous solution which is then de-oxygenated, e.g. by stirring under nitrogen or helium, and/or by bubbling a non-oxygen gas through the solution, etc. In some aspects, the deoxygenated liquid is then removed e.g. by filtering, evaporation, etc. also under anaerobic conditions, to obtain a solid that is substantially free of oxygen. In some aspects, one or more reducing agents is processed (de-oxygenated and solidified) together with the reduced B12 species in the same solution. In other aspects, the reducing agent is processed separately and the two are later combined as solids. In yet other aspects, the solidified, oxidized B12 species is separate from the reducing agent until just before use, e.g. the reducing agent is present in the carrier which is used to dissolve/disperse the reduced B12 species just before administration.

While the reduced B12 species is generally provided as a solid (e.g. crystalline or amorphous) form for dissolution or dispersion just prior to administration, the invention also encompasses concentrated liquid solutions of de-oxygenated, reduced B12 species (which may or may not contain one or more reducing agents) which are mixed with a physiologically acceptable carrier just prior to administration.

Exemplary reducing agents that may be used as components of the compositions described herein are generally physiologically compatible and include but are not limited to: ascorbic acid (Vitamin C), zinc-mercury amalgam, Lindlar catalyst, sodium borohydride, sodium dithionite, formic acid, platinum dioxide, etc. A particularly desirable reducing agent is ascorbic acid, which is physiologically compatible even in high doses. As described above, the one or more reducing agents may be provided in a mixture (e.g. a solidified mixture) with one or more reduced B12 species, or separately as a solid, or separately as a concentrated solution, or already (previously) dissolved in the carrier that is used to dissolve the reduced B12 species just before administration.

The reduced B12 species is mixed with a physiologically acceptable (compatible) de-oxygenated liquid carrier just prior to administration to a subject in need thereof. In the composition that is administered, the concentration of the at least one reduced B12 species is generally in the range of from about 5 mg/mL to about 25 mg/mL, and is usually about 20 mg/mL; and the concentration of the at least one reducing agent is generally in the range of from about 1 mg/mL to about 25 mg/mL, and is usually about 20 mg/mL.

The physiologically acceptable carrier is generally an aqueous liquid and may contain excipients such as, for example, water, saline, dextrose, glycerol, ethanol and the like, or combinations thereof. In addition, the composition may contain minor amounts of auxiliary substances such as wetting or emulsifying agents, pH buffering agents, electrolytes (such as protamine sulfate, disodium hydrogen phosphate, potassium hydrogen phosphate, sodium chloride, or zinc salts), sugars such as lactose, glucose and sucrose, propylene glycol or polyethylene glycol, buffering agents such as magnesium hydroxide and aluminum hydroxide; alginic acid; pyrogen-free water; isotonic saline; Ringer's solution; ethyl alcohol, and phosphate buffer solutions, various preservatives and antioxidants, various pharmaceutically acceptable salts, and the like. The composition of the present invention may contain any such additional ingredients so as to provide the composition in a form suitable for administration. The final amount of a form of reduced Vitamin B12 in a formulation for administration may vary, but in general is from about 1-99%. Still other suitable formulations for use in the present invention can be found, for example in Remington's Pharmaceutical Sciences, Philadelphia, Pa., 19th ed. (1995).

"Pharmaceutically acceptable salts" refers to the relatively non-toxic, inorganic and organic acid addition salts, and base addition salts, of compounds of the present invention. These: salts can be prepared in situ during the final isolation and purification of the compounds. In particular, acid addition salts can be prepared by separately reacting the purified compound in its free base form with a suitable organic or inorganic acid and isolating the salt thus formed. Exemplary acid addition salts include the hydrobromide, hydrochloride, sulfate, bisulfate, phosphate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptonate, lactiobionate, sulfamates, malonates, salicylates, propionates, methylene-bis-.beta.-hydroxynaphthoates, gentisates, isethionates, di-p-toluoyltartrates, methanesulfonates, ethanesulfonates, benzenesulfonates, p-toluenesulfonates, cyclohexylsulfamates and laurylsulfonate salts, and the like. See, for example S. M. Berge, et al., "Pharmaceutical Salts," J. Pharm. Sci., 66, 1-19 (1977) which is incorporated herein by reference. Base addition salts can also be prepared by separately reacting the purified compound in its acid form with a suitable organic or inorganic base and isolating the salt thus formed. Base addition salts include pharmaceutically acceptable metal and amine salts. Suitable metal salts include the sodium, potassium, calcium, barium, zinc, magnesium, and aluminum salts. The sodium and potassium salts are preferred. Suitable inorganic base addition salts are prepared from metal bases which include sodium hydride, sodium hydroxide, potassium hydroxide, calcium hydroxide, aluminum hydroxide, lithium hydroxide, magnesium hydroxide, zinc hydroxide and the like. Suitable amine base addition salts are prepared from amines which have sufficient basicity to form a stable salt, and preferably include those amines which are frequently used in medicinal chemistry because of their low toxicity and acceptability for medical use. ammonia, ethylenediamine, N-methyl-glucamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)-aminomethane, tetramethylammonium hydroxide, triethylamine, dibenzylamine, ephenamine, dehydroabietylamine, N-ethylpiperidine, benzylamine, tetramethylammonium, tetraethylammonium, methylamine, dimethylamine, trimethylamine, ethylamine, basic amino acids, e.g., lysine and arginine, and dicyclohexylamine, and the like.

Methods

The invention also provides methods of treating a subject who has experienced or is likely to have experienced CO and/or cyanide poisoning. The methods may include a step of identifying a subject (patient) in need of such therapy, i.e. a step of diagnosing CO and/or cyanide poisoning. In some cases, a history of CO exposure may be provided e.g. exposure to a fire and smoke inhalation, faulty or poorly ventilated burning of fuel in cars or trucks, small engines, stoves, lanterns, grills, fireplaces, gas ranges, or furnaces, exposure to automobile exhaust, or a deliberate CO exposure (e.g. a suicide or murder attempt), etc. CO poisoning may present much like an acute viral illness, with symptoms such as headache (most common), dizziness, malaise, weakness, upset stomach, vomiting, chest pain, and confusion, and (if the exposure is large enough) loss of consciousness. Because current methods of testing for CO poisoning are somewhat unreliable and results and symptoms can vary widely among patients, any time a patient is suspected of having CO toxicity it is recommended that a blood sample be sent for oximetry analysis immediately and the patient should be placed on 100% $O_2$ by a non-rebreather mask. If a case of suspected CO poisoning is confirmed, then additional tests are generally ordered, including arterial blood gas (to check for acidosis), ECG (to check for dysrhythmias) and cardiac biomarkers (to check for myocardial injury).

Similarly, cyanide poisoning presents in many forms. Industrial intoxications occur due to extensive use of cyanide compounds as reaction products. Smoke inhalation, a polyintoxication, is most often responsible for domestic cyanide poisonings. Signs of cyanide poisoning include headache, vertigo, agitation, confusion, coma, convulsions and death. Definitive laboratory confirmation is generally delayed. Elevated plasma lactate, associated with cardiovascular collapse, should suggest cyanide intoxication. Immediate treatment includes 100% oxygen, assisted ventilation, decontamination, correction of acidosis and blood pressure support. According to the present invention, the compositions described herein are also advantageously administered as "immediate treatment".

The present invention provides a frontline technology for treating CO and/or cyanide poisoning or suspected CO and/or cyanide poisoning by administering the compositions described herein. Administration may be in addition to $O_2$ therapy, or may replace $O_2$ therapy. Generally, administration of the compositions described herein should be carried out as soon as possible after the poisoning event, e.g. preferably within minutes, or hours. A single dose or multiple doses may be administered, usually while the patient is being monitored on an ongoing basis to determine whether there is a need for additional treatment.

Generally, the amount of reduced B12 species that is administered is in the range of from about 5 mg/mL to about 25 mg/mL, and is usually about 20 mg/mL and the amount of reducing agent that is administered is in the range of from about 1 mg/mL to about 25 mg/mL, and is usually about 20 mg/mL, depending on the age, weight, etc. of the victim. This amount of the drug (active agent(s)) is generally administered in a volume of from about 100 mL to about 250 mL, depending on the mode of delivery, e.g. injection volumes may be lower than IV volumes. 5 grams of B12 species and up to 5 grams of the reducing agent are dissolved in 100 mL to 200 mL of diluent. In exemplary embodiments, about 5 grams of i.v. hydroxocobalamin or cobinamide is infused over about a 10 minute period of time. Frequency of delivery is typically 2 doses in 24 hours. Medication may be delivered again within about 15 minutes of the first infusion, or re-administration may be delayed until the patient show signs of deterioration requiring a second dose. The maximum cumulative dose is about 10 grams within 24 hours. The drug is intended to be administered immediately (or as soon as possible) following exposure to carbon monoxide, but it may be administered anytime within the first 24 hours following the exposure.

The compositions may be administered in vivo by any suitable route that allows introduction into the blood stream of a recipient without exposing the composition to oxygen. Generally, such methods involve injection e.g. intravenous or intramuscular administration.

In addition, the compositions may be administered in conjunction with other treatment modalities such as administration of $O_2$ therapy and optionally other CO or cyanide scavenging agents (e.g. hydroxocobalamin, di-cobalt EDTA, methaemoglobin-inducers, sodium thiosulphate, etc.

CO and/or cyanide poisoning can have many untoward ramifications beyond the initial symptoms, including heart damage, neurological damage, kidney damage, muscle damage, atherosclerosis, eye damage, etc. The methods disclosed herein may also be used to prevent or at least lessen the severity or length of such conditions.

In addition, CO and/or cyanide poisoning can result in the generation of NO and associated untoward complications, and the compositions provided herein can also be used to scavenge NO. In addition, elevated NO levels can occur as a result of coronary artery bypass surgery, causing vasoplegia, a postperfusion syndrome characterized by low systemic vascular resistance and a high cardiac output. Vasoplegic syndrome is defined as low systemic vascular resistance (SVR index <1,600 dyn·sec/$cm^5$/$m^2$) and high cardiac output (cardiac index >2.5 l/min/$m^2$) within the first 4 postoperative hours. Blood pressure can drop to dangerously low levels and death may ensue. Without being bound by theory, this is thought to be caused by dysregulation of nitric oxide/nitric oxide synthase pathways. There is some evidence to support the use of methylene blue in the treatment of this condition. However, methylene blue can cause conditions known as "Serotonin Syndrome" when given to patients taking certain antidepressants (includes SSRIs and MAOIs). Serotonin Syndrome can be fatal and causes numerous complications, particularly in surgical patients. Unfortunately, due to the nature of the disease, many patients with heart problems who need surgery are also on an antidepressant, making the use of methylene blue extremely risky. Hydroxocobalamin alone has been shown to react with nitric oxide and cause an increase in blood pressure, but the effect is not as strong or as long lasting as that of methylene blue. However, the combination of reduced B12 species plus a reducing agent as described herein (e.g. hydroxocobalamin plus ascorbic acid) provide an effective alternative or adjunct scrubbing treatment for decreasing NO levels in blood. In some embodiments, the compositions are administered before surgery to prevent the occurrence of elevated NO; in other embodiments, the compositions are administered after surgery (usually immediately afterwards and/or during the 4-hour post-operative window). However, in some embodiments, follow-up doses of the compositions may also be administered. In further aspects, the compositions are administered ex vivo, i.e. the blood of the patient is scrubbed as is circulates extracorporeally through a heart-lung machine or "pump", e.g. by passing the blood through a chamber or filter saturated with a composition of the invention, or by adding the composition to the circulating blood.

Kits

In some aspects, kits and containers for administering the compositions described herein are provided. The containers are designed to house the active agent(s), generally in solid form, that is/are to be administered and the physiological compatible carrier, generally in liquid form, and generally de-oxygenated. The components are positioned in the container in a manner which prevents mixing of the active agent(s) and the carrier until just before administration. In other words, the active agent is sequestered, isolated, partitioned, etc. apart from the liquid carrier, but in a manner that allows facile mixing and dissolution of the active agent in the carrier immediately prior to administration to a subject. In addition, the active agent and carrier are both stored and mixed under anaerobic conditions so that before and during mixing, oxygen does not enter the system, and the mixed solution is also not exposed to oxygen prior to or during administration.

In an exemplary aspect, such containers comprise an outer compartment for containing a liquid carrier and a compartment for containing a solid (or concentrated) active agent. "Active agent" as used herein refers to at least one reduced B12 species and, optionally, at least one reducing agent. If the reduced B12 species and the at least one reducing agent are not combined into a single preparation, they may be housed in separate compartments. In some aspects, the compartment or chamber for containing a liquid carrier may be or may resemble a standard flexible intravenous bag, many of which are known in the art, and may be formed from e.g. UV shielded material such as plastic, foil, etc. Generally, the outer chamber is impermeable to UV light and oxygen. The compartment or chamber for containing a solid active agent may be a smaller bag, sac or pouch that is located within the IV bag, either free-floating or permanently affixed at a location within the bag. The smaller interior bag is generally also impervious to UV light and is impervious to the liquid in the outer chamber; thus the solid active agents are kept dry and in solid form during storage. Just prior to use, the inner sac is ruptured (e.g. by manual pressure exerted by the user "squeezing" the inner sac with fingers, or by another means of imposing pressure; or by some other mechanism, e.g. by puncturing the sac with a needle that is introduced via a one-way or self-sealing port). As a result, the contents of the inner sac are released and mixing of the active agents and carrier ensues. Mixing may be facilitated by inverting the sac and/or otherwise manipulating the contents to ready the mixture for administration.

Figure 8A:
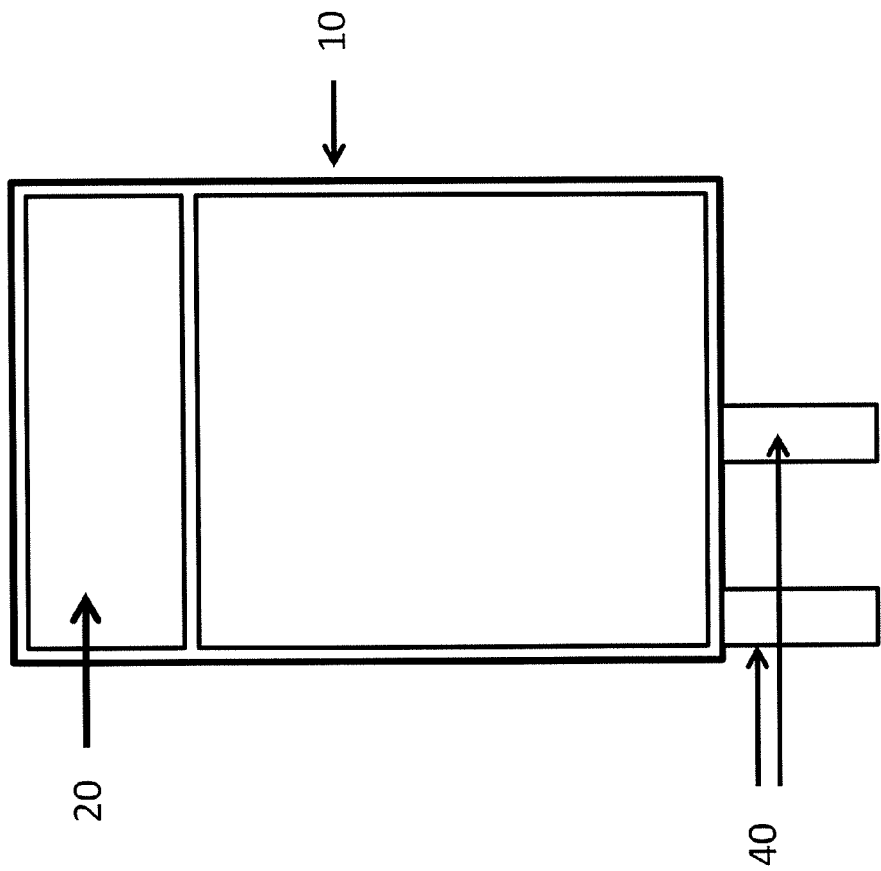
FIG. 8A-E. Schematic illustration of exemplary devices for delivery of Vitamin B12 compounds to treat CO (and other) poisoning. A, modified intravenous bag with internal pouch for B12 compound; B, modified intravenous bag with external compartment for B12 compound; C, modified intravenous bag with external compartment for B12 compound and comprising a cap; D, modified "syringe" style device; E, modified "syringe" style device with a gas driven plunger.

This exemplary aspect is illustrated schematically in FIG. 8A, which shows chamber 10 for containing a liquid carrier and internal chamber 20 for containing a solid active agent. Internal chamber 20 may also be formed from flexible or malleable material and is rupturable by pressure. At least one (optional) infusion/sampling port 40 is present and leads from the interior of chamber 10 and into the surrounding environment (e.g. into an IV line). Port 40 may functions as i) a means of egress of the mixed solution, e.g. into an IV drip line, or ii) a means of ingress for a needle, e.g. to withdraw the mixed solution, etc. It is noted that if the reduced B12 species and the at least one reducing agent are separate preparations, e.g. separate solids, then an additional internal chamber may also be present so the B12 species and reducing agent are housed separately.

Other configurations of the container are also possible. For example, in another aspect, the liquid carrier is contained within a flexible sac such as an IV bag and the solid active agents are contained within an external chamber that is substantially permanently affixed or attached to an outer surface of the flexible sac. An exemplary configuration of this type is presented in FIG. 8B. As can be seen, external chamber 30 is positioned outside and on an external surface of chamber 10. The walls of external chamber 30 are generally more rigid than those of chamber 10 (or internal chamber 20, see above) and may be formed, for example, from opaque or brown glass or plastic, which is generally UV impenetrable. External chamber 30 comprises inner seal/connection tubing 50 that connects chamber 10 to external chamber 30, separating the contents of chamber 10 from that of external chamber 30. Inner seal/connection tubing 50 is susceptible to rupture (breakage, puncture, etc.) by manipulation, e.g. by twisting, rotating, depressing, extending, etc. For example, rotation of inner seal/connection tubing 50 causes the seal between chamber 10 and external chamber 30 to break, creating a passage for the entry of carrier solution from chamber 10 into external chamber 30 and vice versa. Mixing is facilitated e.g. by inverting the container at least once, and agitating or otherwise manipulating the contents to cause mixing. The entire container may be righted to initiate fluid flow. It is noted that if the reduced B12 species and the at least one reducing agent are separate preparations, e.g. separate solids, then an additional external chamber may also be present so the B12 species and reducing agent are housed separately.

Figure 8B:
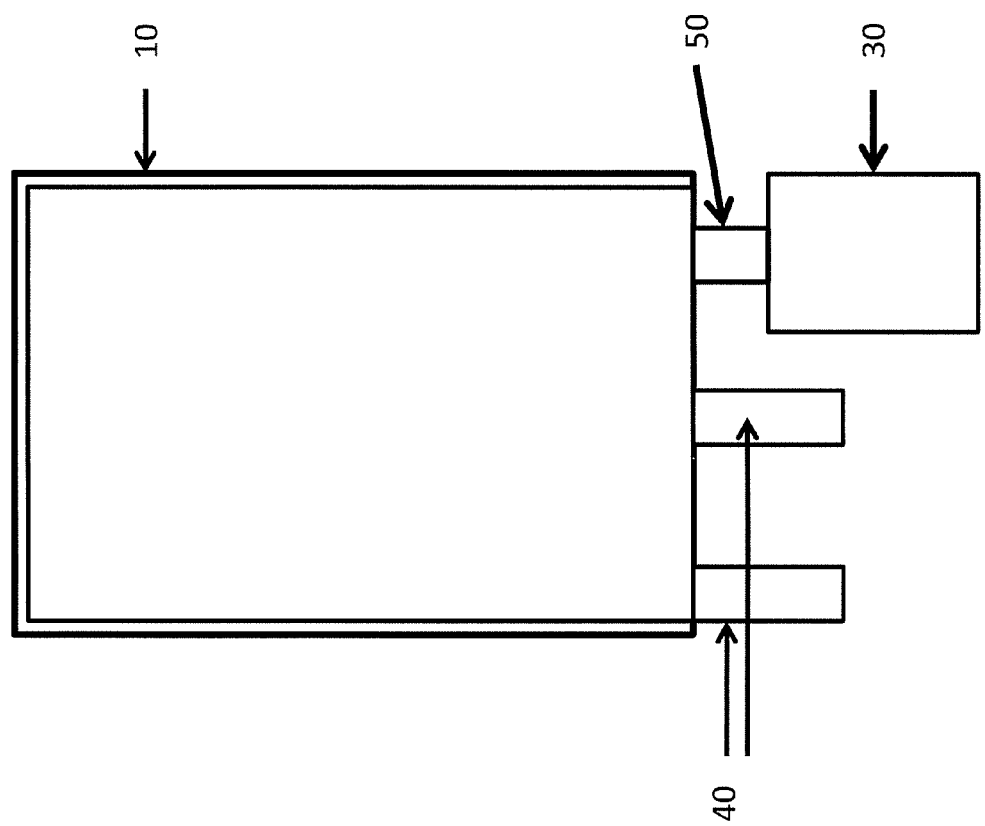
Figure 8C:
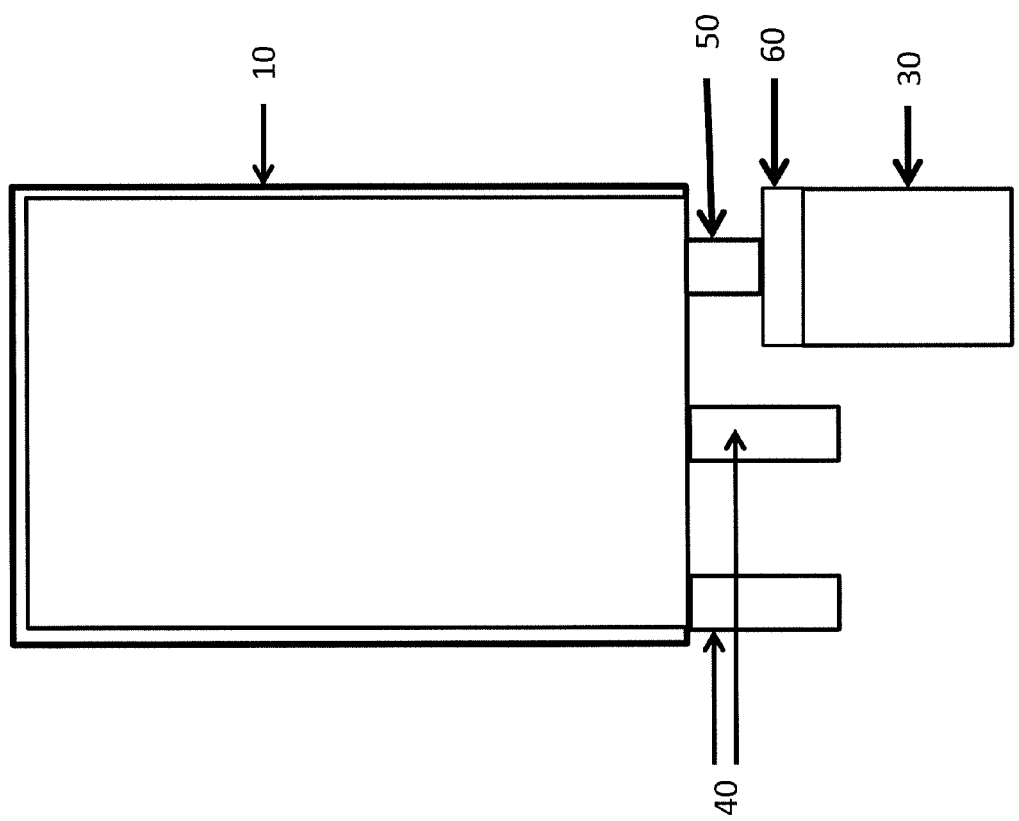

In an additional embodiments, shown in FIG. 8C, the delivery device is similar to that shown in FIG. 8B but also comprises cap 60 interposed between external chamber 30 and inner seal/connection tubing 50. Manipulation of cap 60 (e.g. twisting, rotating, etc.) may break the seal between chamber 10 and external chamber 30, creating a passage for the entry of carrier solution from chamber 10 into external chamber 30 and vice versa. Alternatively, cap 60 may comprise a protrusion that contacts and ruptures the seal upon depression, rotation, etc.

Figure 8D:
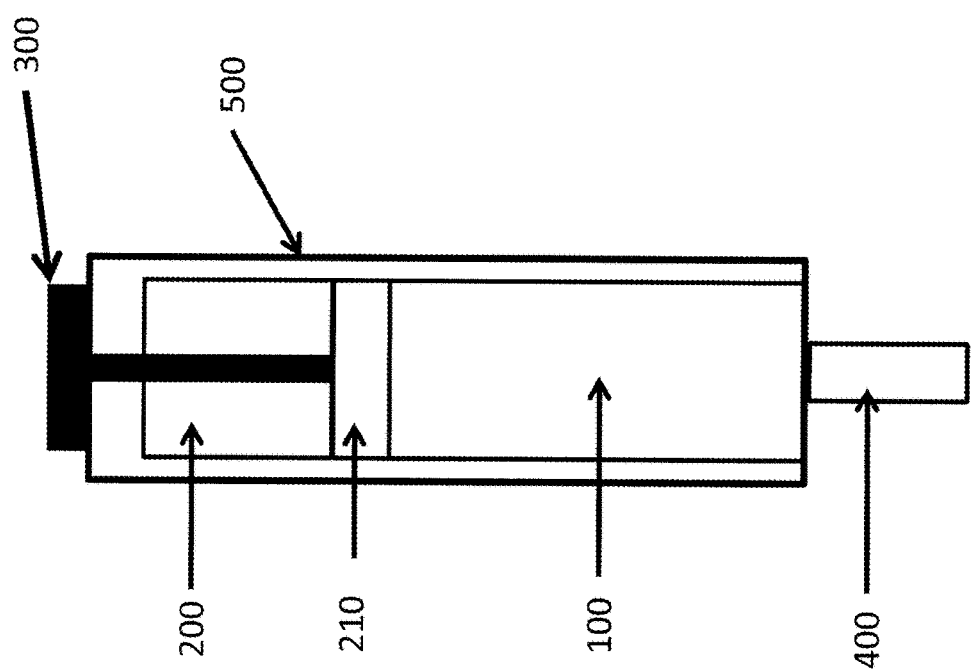

Other embodiments of a container include those based on a syringe, as illustrated in FIG. 8D. In this figure, the barrel of a cylinder with rigid walls such as e.g. a syringe is divided into separate chambers for containing the carrier and active agent. As schematically illustrated, syringe barrel 500 (generally made from gas impermeable and UV shielded plastic, or metal) contains chamber 100 which contains the liquid carrier and chamber 200 which contains the solid active agents. Chambers 100 and 200 are separated by seal 210. Just prior to use, seal 210 is broken by e.g. twisting or depressing outer cap 300 so as to break seal 210. For example, outer cap 300 may comprise a protrusion that, upon manipulation, contacts seal 210 and punctures it. Element 400 represents a Luer lock adaptor for attachment of a needle, or, optionally, a needle for injection or direct connection to an intravenous line previously inserted.

Figure 8E:
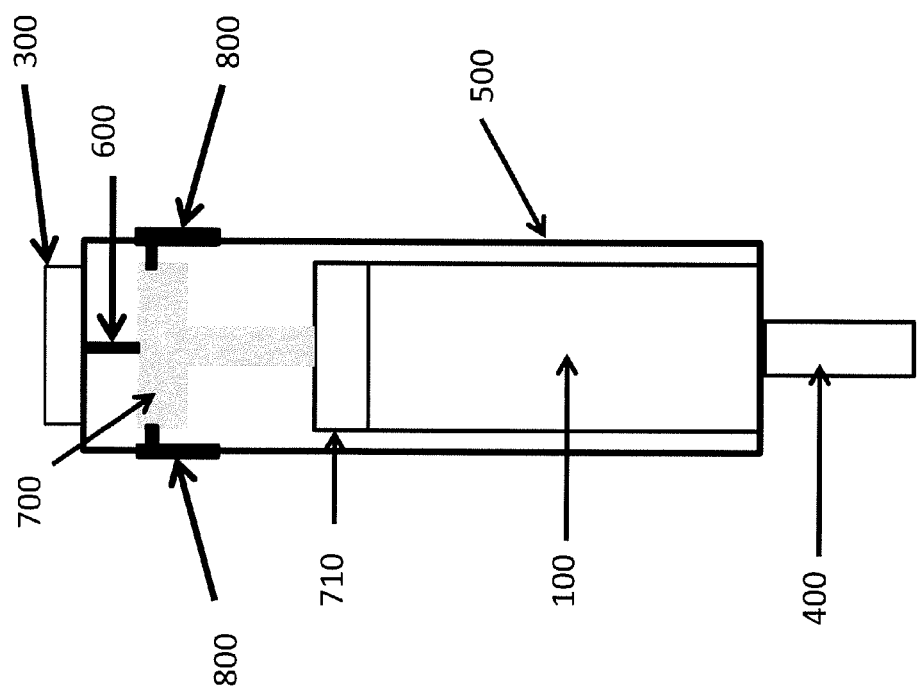

An alternative embodiment is illustrated in FIG. 8E, where outer cap and plunger 300 comprises a gas driven plunger which is locked in place during storage by retention screw or tether 600. In this embodiment, the components (carrier, Vitamin B12 compound, at least one reducing agent) may be pre-mixed and contained within chamber 100, and the syringe is pressurized with an inert gas. Twisting or depressing outer cap and plunger 300 breaks or unlocks retention screw/tether 600 which allows drive plunger 700 to move, displacing inner seal/plunger 710 downward and thereby delivering the medication via injection tip 400. If the gas drive mechanism fails to deliver the medication, release is activated by squeezing the manual override sliders 800 located on each side of syringe barrel 500.

In all aspects, materials of which the containers are made are generally impermeable to UV light, and the content of each chamber is generally free of oxygen, e.g. the chambers are kept under nitrogen or helium gas pressure. The contents (e.g. the liquid carrier and the active agent(s)) are generally de-oxygenated (e.g. using $N_2$ or He gas) prior to use and, in the case of the reduced Vitamin B12 components, are generally produced, stored and maintained under anaerobic conditions so as to maintain the desired oxidation state.

The present invention is particularly advantageous because, unlike $O_2$ therapy, the kits described herein are lightweight and compact and, in some aspects, do not require highly specialized equipment for administration. Some embodiments are essentially modified syringes, and others require only that a sterile needle be provided. In other aspects, the compositions are provided by IV administration, but these requirements are also minimal, so long as the needle can be affixed to the subject at a suitable location and the IV bag can be elevated sufficiently to maintain a suitable rate of delivery. Thus, the kits are readily deployed e.g. by emergency medical technicians at the scene of CO exposure.

Before exemplary embodiments of the present invention are described in greater detail, it is to be understood that this invention is not limited to particular embodiments described, as such may, of course, vary. It is also to be understood that the terminology used herein is for the purpose of describing particular embodiments only, and is not intended to be limiting.

Where a range of values is provided, it is understood that each intervening value between the upper and lower limit of that range (to a tenth of the unit of the lower limit) is included in the range and encompassed within the invention, unless the context or description clearly dictates otherwise. In addition, smaller ranges between any two values in the range are encompassed, unless the context or description clearly indicates otherwise.

Unless defined otherwise, all technical and scientific terms used herein have the same meaning as commonly understood by one of ordinary skill in the art to which this invention belongs. Representative illustrative methods and materials are herein described; methods and materials similar or equivalent to those described herein can also be used in the practice or testing of the present invention.

All publications and patents cited in this specification are herein incorporated by reference as if each individual publication or patent were specifically and individually indicated to be incorporated by reference, and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual dates of public availability and may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as support for the recitation in the claims of such exclusive terminology as "solely," "only" and the like in connection with the recitation of claim elements, or use of a "negative" limitations, such as "wherein [a particular feature or element] is absent", or "except for [a particular feature or element]", or "wherein [a particular feature or element] is not present (included, etc.) . . . ".

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

EXAMPLES

Example 1

Evaluation of Injectable Reduced Hydroxocobalamin as an Antidote to Acute Carbon Monoxide Poisoning Abstract Current management of acute inhalational carbon monoxide (CO) toxicity includes hyperbaric or normobaric $O_2$ therapy. However, efficacy has not been established. The purpose of this study was to establish therapeutic proof of concept for an exemplary, novel injectable antidote of reduced hydroxocobalamin (B12r) together with the reducing agent ascorbic acid, as demonstrated by clinically-significant increase (>500 ppm) in $CO_2$, production, reduced carboxyhemoglobin (COHgb) half-life (COHgb $t_{1/2}$), and increased cerebral $O_2$ delivery and attenuation of CO-induced microglial damage in a preclinical rodent model of CO toxicity.

Background

Carbon monoxide (CO) is the leading cause of poisoning death and a significant cause of long-term morbidity, especially delayed neurological sequelae. Conventional treatment with 100% $O_2$ acts to displace CO from Hb. However, $O_2$ must be administered over many hours, and blood Hb-CO levels are poorly correlated with clinical outcomes.

We propose a solution of hydroxocobalamin (OHCbl), an FDA-approved antidote for cyanide poisoning and ascorbic acid (vitamin C), a safe and powerful reducing agent. Other chemically-reduced forms of OHCbl ($B_{12r}$) have been demonstrated to convert CO to $CO_2$ in simple solutions in vitro'. We hypothesized $B_{12r}$ could also facilitate conversion of CO to $CO_2$ in blood, resulting in the rapid reduction of the total body CO load via respiratory off-gassing of $CO_2$. The speed of this reaction should avert or reduce CO-induced DNS by early prevention of inflammatory changes associated with elevated intracellular CO levels. Antidote effectiveness can therefore be defined as both the demonstration of either irreversible binding or conversion of CO, and clinically-significant reduction of delayed neurological and cognitive deficits. We performed a two-part test of this hypothesis to establish therapeutic proof of concept: (1) in vitro CO removal from blood as demonstrated by a clinically-significant increase (>500 ppm) in $CO_2$ production and reduction of carboxyhemoglobin (COHgb) half-life ($t_{1/2}$), and (2) in vivo demonstration in a preclinical rodent model of cognitive function, increased cerebral oxygen delivery, and attenuation of CO-induced microglial damage.

Methods

Reduced OHCbl ($B_{12r}$) was produced by combining 300 mg analytical grade hydroxocobalamin (OHCbl) and 300 mg ascorbic acid (AA) (Sigma-Aldrich, St. Louis, Mo.) in 5 mL deoxygenated 0.9% NaCl solution ($NS_{deox}$) in 100% $N_2$ environment to prevent auto-oxidation[6]. The $B_{12r}$ generated in this fashion was not separated from the ascorbic acid. The formation of $B_{12r}$ was verified by Resonance Raman spectroscopy, however these results are not discussed in this manuscript.

In vitro experiments: $B_{12r}$-mediated CO reduction in blood. IRB-exempt waste human venous blood was obtained from VCU Apheresis clinic; 600 mL was collected into standard blood collection bags and anti-coagulated with 70 mL of CPD-A1. Blood was used within 24-48 hours following collection. Blood was circulated through a closed-loop hollow-fiber membrane oxygenator (Pediatric QUADROX-ID®, Maquet, Hirrlingen, Germany) and roller pump (STOCKERT/SHILEY®, Soma Technology Inc, Bloomfield Conn.) at 250 mL/min, and maintained at 37° C. with a countercurrent water-flow heat exchanger (DC 10, Thermo Haake, Fisher Scientific). The system was equilibrated with medical air (20-22% v/v $O_2$; <400 ppm $CO_2$; 78-80% v/v $N_2$) then 'poisoned' with 6000 ppm CO in research grade air (0.5838% v/v CO, balance air) for 20 minutes; all air flow rates were 178 mL/min. The system was then injected with 5 mL of either $B_p$, or one of three negative controls: $NS_{deox}$, AA (350 mg in 5 mL $NS_{deox}$), or $B_{12a}$ (350 mg OHCbl in 5 mL $NS_{deox}$). $CO_2$ concentration (volume %) was sampled at 10 Hz (BIOPAC Inc., Galeta Calif.) over 30 minutes from the time of $B_{12r}$ injection or when carboxyhemoglobin (COHgb) concentration reached 50%; in-flow gas was then switched back to medical grade air. Gas-out concentration of $CO_2$ was continuously measured at 10 Hz for 30 min post-infusion. Signals were amplified (CO2100C interface), and analog-digital conversions were performed online (ACQKNOWLEDGE™ v. 4 software; BIOPAC Systems, Goleta, Calif.). Median $CO_2$ concentration for each solution was calculated from the normalized area under the curve (AUC) of the $CO_2$-time response curves.

Confirmation that $CO_2$ was derived from $B_{12r}$-mediated conversion of CO (and not an unidentified exogenous source) was obtained by radiocarbon tracing in separate trials. Twenty-mL of $^{13}C$ labeled CO (Cambridge Isotope Laboratories, Tewksbury, Mass.) was injected into the system 30 min prior to infusion with 5 mL $B_{12R}$. Gas samples were taken at baseline and 20 min post-infusion; the difference in the $^{13}CO_2/^{12}CO_2$ ratio between baseline and post-$B_{12r}$ infusion was quantified by infrared spectral analysis (POCONE®, Otsuka Electronics Co., Japan).

Carboxyhemoglobin (COHgb) concentrations were determined by Resonance Raman (RR) spectroscopy. Blood was treated with either high-flow atmospheric pressure $O_2$ alone, or with a combination of high-flow $O_2+B_{12r}$ solution. Blood samples were obtained at baseline and every 10 min for 120 min RR spectra of COHgb were obtained for 20 μL sub-samples sealed into melting-point capillary tubes; excitation lines were obtained from a 406.7 nm krypton-ion laser excitation source (Coherent Saber) and attenuated output power of 0.07-0.08 mW, collected using a 600-mm single-grating monochromator, and imaged using a back-illuminated CCD camera (Python CCD, Princeton Instruments, Trenton, N.J.). Scans were completed in 3-5 min. COHgb half-life $t_{1/2}$ was calculated as $(\ln 2)/\lambda$, where $\lambda$ is the rate constant for the decay function $P_t=P_0 \cdot \exp(-\lambda \cdot t)$; $P_t$ is peak height at time t, and $P_0$ is initial peak height. Calculations were performed in PROC NLIN (SAS 9.4).

In Vivo Studies

Ethics statement and animals. This study was approved in advance by the Institutional Animal Care and Use Committee (IACUC) of Virginia Commonwealth University (IACUC Protocol # AD10000569), and conforms to the Public Health Service Policy on Humane Care and Use of Laboratory Animals (2002). All rats were obtained from Harlan Laboratories (Indianapolis, Ind.) at 5-8 weeks of age. Before experimentation, animals were housed in pairs in ventilated cages and maintained at 25° C. and 12 L:12D, with ad lib access to food (commercial rat chow) and water. Animals were weighed daily for a minimum of 7 days prior to surgical procedures.

Brain oxygenation. The experimental design was a 2×2 factorial on the factors exposure (medical air SHAM or CO) and intervention (NS or $B_{12r}$). Thirty male adult Sprague-Dawley rats (mass 315-370 g) were randomly allocated to one of four groups (SHAM-NS, SHAM-$B_{12r}$, CO-NS, CO-$B_{12r}$) with EXCEL random numbers algorithm; 10 animals were allocated to each CO group, and 5 to each sham group.

All surgical procedures were aseptic. Animals were anesthetized with isoflurane (4% for induction, 2% for maintenance, balance medical air). Core temperature was monitored with a rectal probe and maintained at 36-38° C. for the duration of each trial with a thermostatically-controlled feedback heating blanket (Harvard Apparatus, Holliston, Mass.). The head was stabilized in a stereotaxic frame, the skull exposed along the midline, and two 2-mm burr holes were drilled 1-mm posterior to bregma and 3-mm lateral to midline. The dura mater was gently incised to allow placement of calibrated LICOX® brain oxygenation (CC.1.R.) and temperature (CB.8) probes (Integra Neuroscience, Plainsboro, N.J.); probes were inserted 2.3 mm into the parenchyma. Animals were allowed to stabilize for 30 min. Animals were then exposed for 30 minutes to either 2500 ppm CO or medical air, followed by a single intraperitoneal dose of intervention solution, either $B_{12r}$ at 100 mg/kg or the weight-based equivalent volume of NS (2 mL/kg); total volumes were 0.6-0.85 mL. Brain oxygenation $Pb_tO_2$ was recorded every 5 min for 60 min post-infusion. Animals were then euthanized under deep anesthesia with sodium pentobarbital (EUTHASOL®, 40 mg/kg IV, Virbac Animal Health, Fort Worth, Tex.).

Post-infusion change of $Pb_tO_2$ over time t for both CO-exposure groups was described by the parametric nonlinear mixed-effects model $Pb_tO_2=a \cdot [1-b \cdot \exp(-k \cdot t)]+Z(t)$, where a is the maximum value of $Pb_tO_2$, b is a scaling parameter, k is the rate constant, and Z(t) describes the random effects component for each animal. Differences between control and antidote were evaluated by contrasts on each parameter estimate. Primary outcome was time to achieve $Pb_tO_2$ of 25 mmHg ($\tau_{25}$); this is the approximate hypoxic brain tissue threshold established for humans[8], and is approximately 75% of baseline $Pb_tO_2$ levels (33-35 mmHg) for rats. Calculations were performed in PROC NLMIXED (SAS 9.4).

Spatial learning. Forty-two male young adult Long-Evan rats (average initial weight 219 g; average terminal weight 300 g) were randomly assigned (RANDOM.ORG) to one of three treatment groups: medical air only (SHAM, n=12), CO exposure with NS infusion (CO—NS, n=19) or CO-exposure with $B_{12r}$ antidote infusion (CO—$B_{12r}$, n=21). CO-exposed animals received 2500 ppm CO (0.25% CO, 27% $O_2$, balance $N_2$) for 60 min, followed by 6000 ppm CO (0.6% CO, 27% $O_2$, balance $N_2$) for a 10 min, or until loss of righting response; animals were then removed from the exposure chamber and immediately administered antidote or NS (2 mL/kg IP, 0.6-0.8 mL) Animals were allowed to recover in temperature-controlled recovery cages until they regained normal response to stimuli, and then returned to their primary housing cage.

Twenty-four hours following experimental exposures described above, animals began four-stage Morris Water Maze (MWM) testing. Deficits in MWM performance are associated with damage to specific regions of the brain involved with spatial navigation and learning, such as the hippocampus[9,10]. Tests were conducted in a standard water maze pool (diameter 183 cm; depth 63.5 cm) with a submerged platform 2.5 cm below the water surface; non-toxic white paint was added as a water opacifier. The four test stages occurred on post-injury days 1, 3, 6, and 8. Each stage consisted of blocks of four swimming trials of 60 sec each, starting from one of four randomly-chosen compass positions, with a ten-minute inter-trial rest interval. Platform location was constant between trials, but moved to a new location for each stage. Testing was performed by a technician blinded to group assignment, and not involved with injury protocol or analyses. Animal movements were tracked and quantified with a ceiling-mounted video camera and computer-assisted tracking software (Med Associates Inc., St Albans, Vt.). Spatial learning was quantified by path efficiency (PE, %) estimated as the straight-line distance from start to platform divided by observed total swim path length. Differences between treatments for median PE were assessed by nonlinear mixed-model analysis (PROC NLMIXED, SAS 9.4)[11].

Immunohistochemistry Nine male Long-Evans rats (300-350 g), three from each of the above groups were killed on post-injury-day 10 with Euthasol (150 mg/kg IP), and fixed with 4% formalin via transcardial perfusion. Neuronal tissue was preserved in 4% formalin for 24 hours, then sectioned into 40 μm sections from bregma +3 to −7 on a Leica VT1000® vibratome. Sections were simultaneously blocked and incubated with primary antibodies at 4° C. for 24 h utilizing a double-staining protocol for ionized calcium-binding adapter molecule-1 (IBA-1) (Wako Chemicals USA, Richmond, Va.) and glial fibrillary acidic protein (GFAP) (Vector Laboratories, Burlingame, Calif.). Tissue sections were then rinsed and incubated at room temperature for 60 min with secondary antibodies (DyLight-488 and DyLight-549) (Vector Laboratories, Burlingame, Calif.) specific to the IBA-1 and GFAP antibodies. Control sections using only single antibodies and blocking solutions were prepared to examine non-specific binding. After curing for 24 hours sections were examined with a Zeiss LSM 710 laser scanning confocal microscope. Cell counts were obtained using an automated cell counting routine in NIH ImageJ. Microglial activation state was determined by morphometric analysis based on cell body size, process length, and thickness[12]. Astrocyte status was determined by manual morphometric analysis.

Results

In vitro studies Median $CO_2$ concentration for $B_{12r}$ averaged 1170 ppm, compared to <200 ppm for controls. This represents a five- to eight-fold increase in the gas-out concentration of $CO_2$ (FIG. 1). We detected a 16.7% increase in the $^{13}CO_2/^{12}CO_2$ ratio over baseline with $B_{12r}$ infusion whereas infusing a standard sample with $^{13}CO$ caused no interference in the analysis of $^{13}CO_2$. COHgb half-life $t_{1/2}$ was 33 (95% CI 27, 42) min under $O_2$ alone, but was reduced to 18 (95% CI 15, 21) min with $B_{12r}$ infusion, a difference of 15 min (p<0.001).

Figure 2:
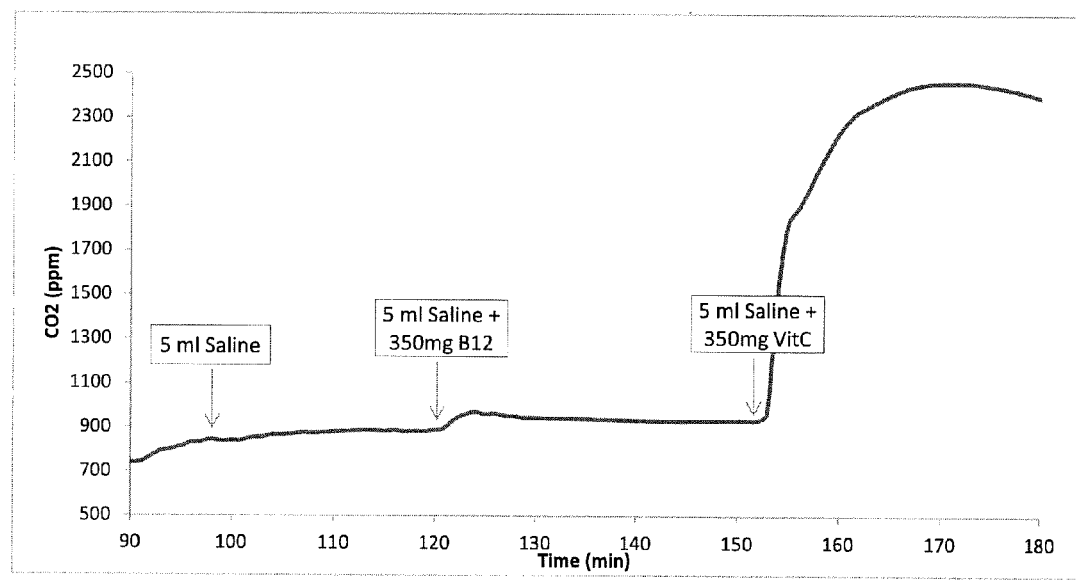
FIG. 2. Difference in the activity of the mixture of ascorbic acid and OHCbl (reduced versus non-reduced OHCbl) for reacting with CO in-vitro. Neither the injection of NS, nor the injection of OHCbl resulted in a significant (i.e., <500 ppm) change in the gas-out concentration of $CO_2$. The subsequent administration of ascorbic acid, resulted in a 3-fold increase in the gas-out concentration of $CO_2$ with a median increase of 1100 ppm over baseline. Injection of the solution of pre-mixed OHCbl and ascorbic acid into blood containing 45-55% COHgb resulted in a 3-4 fold increase in the gas-out concentration of $CO_2$.

Serial Injections:

We performed the NS and the OHCbl negative controls in a serial fashion, in order to assess and demonstrate the unique nature of the combination of ascorbic acid and OHCbl. After forming COHgb using the closed-loop circulation system we injected the NS, followed by injection of the OHCbl, and then by injection of ascorbic acid at 30-minute intervals. FIG. 2 demonstrates the difference in the activity of the mixture of ascorbic acid and OHCbl (reduced versus non-reduced OHCbl) for reacting with CO in-vitro. Neither the injection of NS, nor the injection of OHCbl resulted in a significant (i.e., <500 ppm) change in the gas-out concentration of $CO_2$. The subsequent administration of ascorbic acid, resulted in a 3-fold increase in the gas-out concentration of $CO_2$ with a median increase of 1100 ppm over baseline. Injection of the solution of pre-mixed OHCbl and ascorbic acid into blood containing 45-55% COHgb resulted in a 3-4 fold increase in the gas-out concentration of $CO_2$.

In vivo studies $Pb_tO_2$ of both sham-exposure groups of rats averaged 31 (95% CI 28, 35) mmHg throughout the procedure, with no change upon administration of antidote or NS control. CO-exposure induced severe brain hypoxia with a decline in $Pb_tO_2$ to 18 mmHg (95% CI 17, 19 mmHg). After administration of either NS or $B_{12r}$ there was a nonlinear asymptotic increase to baseline levels by the end of the monitoring period (FIG. 2); maximum $Pb_tO_2$ (33 mmHg) did not differ between the two CO-exposure groups (p=0.61) and did not differ from sham groups. However $\tau_{25}$ differed significantly between CO-exposed groups (p <0.0001); $\tau_{25}$ averaged 40 (95% CI 36, 45) min for CO-exposed NS controls, compared to only 12 (95% CI 10, 13) min for CO-exposed $B_{12r}$ animals.

Figure 3:
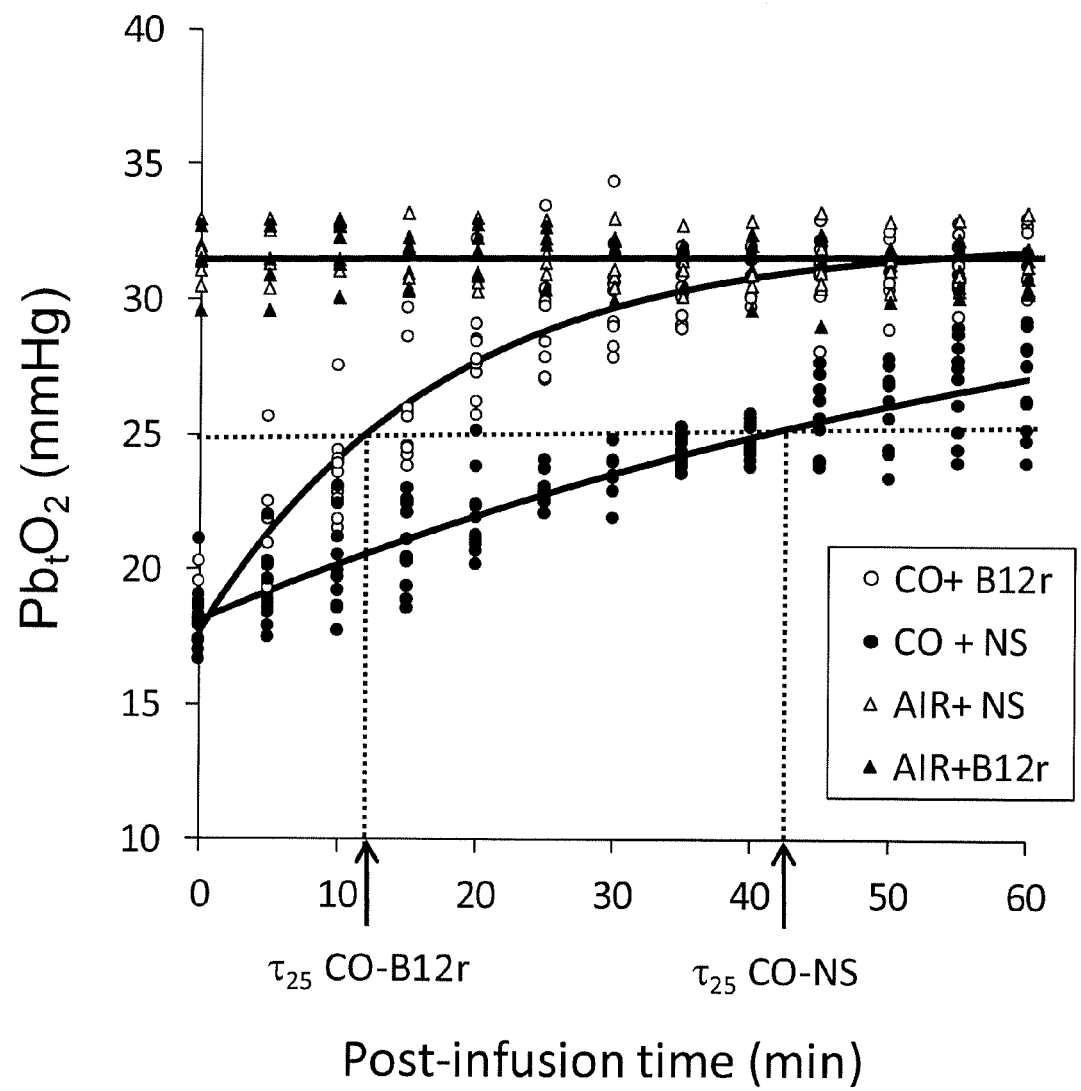
FIG. 3. Brain oxygen tension ($Pb_tO_2$, mmHg) measured in 30 Sprague-Dawley rats exposed to medical air (AIR) or CO, and injected with either saline (NS) or antidote ($B_{12r}$). Solid lines are fitted equations; dotted lines show estimated threshold $\tau_{25}$ for each CO-exposure treatment.

Median path efficiencies obtained from Morris water maze testing are shown in FIG. 3. There were no statistical differences between treatments at any time point (p >0.2) although weak differences in learning trajectories were suggested by examination of medians. Rats exposed to medical air only showed the expected daily increase in path efficiency; efficiencies increased by an average of 8-10% per day over eight days of testing. In contrast, both CO-exposed groups showed a plateau in performance with either no change (Co-B12r) or a modest decline (CONS 7%).

Figure 4:
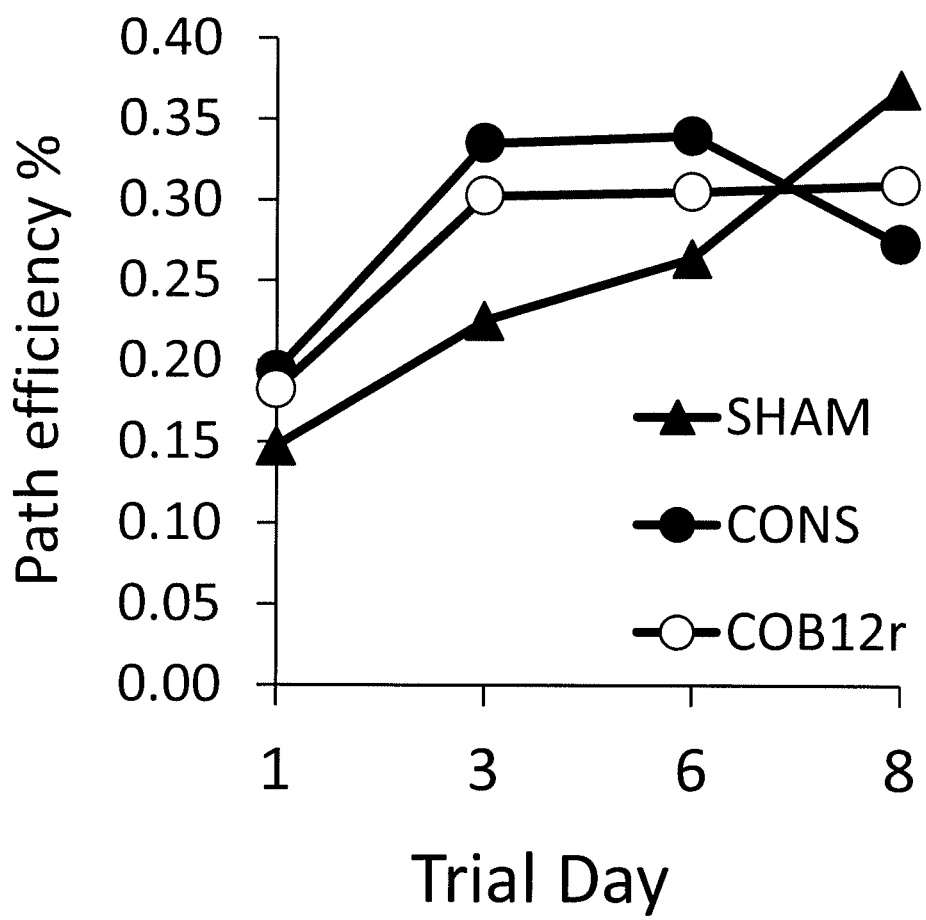
FIG. 4. Median path efficiencies (straight line distance/ observed swim path length) for rats exposed to medical air (SHAM) or CO and injected with either NS (CO-NS) or antidote (CO-B12) and tested in a Morris Water maze over 8 days.
Figure 5C:
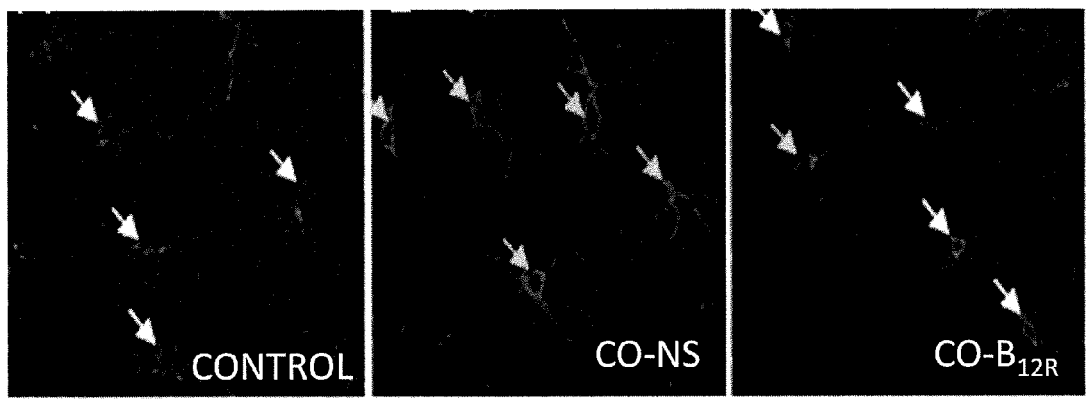
Figure 6E:
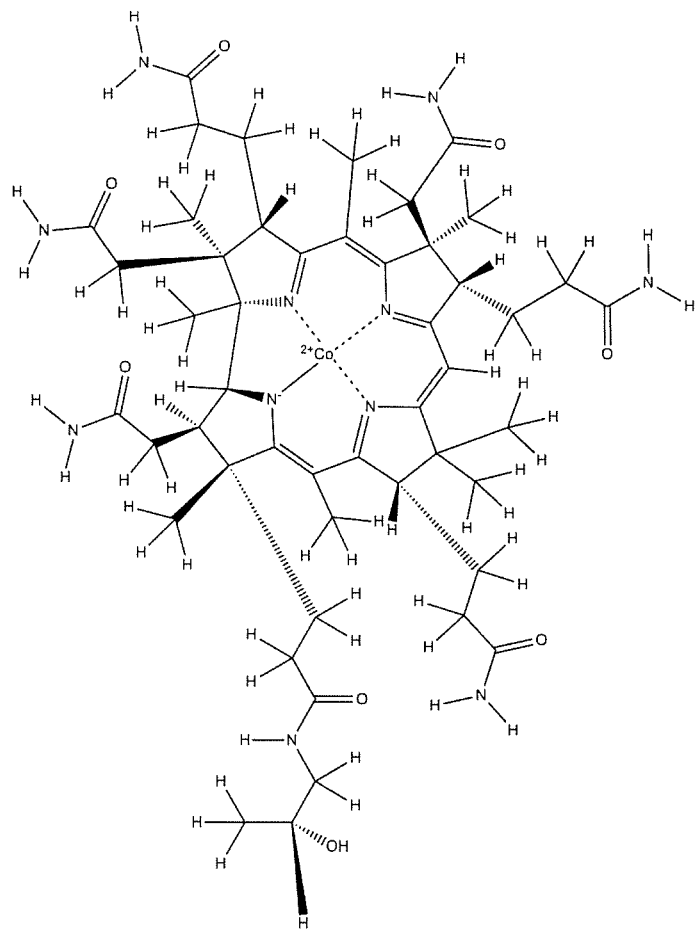

Preliminary immunochemistry data suggest loss in overall cell count (FIG. 4 A), increased demyelination (FIG. 4B) and reduction of microglial activity (FIG. 4 C) associated with CO-exposure; however $B_{12r}$ treatment appeared to partially reverse CO-induced damage. Myelinated axons were abundant in cortical layers 2-5 in control animals compared to CO-exposed animal; however whereas rats exposed to CO showed obvious deficit; CO-exposed rats receiving an immediate single dose of $B_{12r}$ showed partial preservation of myelinated axons (FIG. 4B). CO exposed rats also exhibited microglia with a morphology consistent with activation; cells had enlarged cell bodies and thicker, less-branched processes, compared to microglia of either control or $B_{12r}$ treated rats (FIG. 4C).

Conclusions

Victims of inhalational CO toxicity show a reduction of COHgb half-life from 5 hours on room air to 30-60 min with NBO and only 5 min with HBO. However neither of these interventions has been conclusively demonstrated to reduce the incidence of DNS specifically despite numerous trials, and may be difficult to deploy in a timely way. Our data suggest that the reduced form of hydroxocobalamin, with ascorbic acid as the reducing agent, results in a clinically-significant off-gassing of $CO_2$ levels 5 to 8 times greater than controls, a clinically-significant reduction in COHgb half-life, and evidence of increased brain oxygenation, and amelioration of microglial damage in rat models. These data show a novel synergism of these two compounds when combined at high dose, with the ability to extract CO through conversion to $CO_2$ independently of high-flow or high-pressure $O_2$. Furthermore, both hydroxocobalamin and ascorbic acid are safe and approved for use in humans, even at high doses[13,14]. Reduced hydroxocobalamin thus serves as an injectable antidote for CO toxicity.

Discussion

Schrauzer and Lee demonstrated over 40 years ago that $B_{12r}$ could convert CO to $CO_2$ in simple solution, but failed to demonstrate this reaction in blood[5]. We found that $B_{12r}$ is capable of converting CO to $CO_2$ in blood. We found that $B_{12r}$ has a clinically relevant impact by rapidly increasing brain tissue oxygen tension compared with $O_2$ therapy alone. Finally through a combination of cognitive testing and IHC pathology studies we found evidence to suggest that $B_{12r}$ protects against development of cognitive dysfunction in rats, another clinically relevant effect. DNS from CO poisoning have a variable period of onset after injury, making detection and monitoring difficult. Our cognitive testing model using the Morris Water Maze failed to show a significant difference between groups, but the data suggest that the groups were diverging at the study end-point of 8 days. The delayed neurologic sequelae (DNS) experienced by patients after CO poisoning can occur at any time from 7-270 days following the injury in humans. Our rats were tested on days 1, 3, 6 and 8. DNS is a complex injury with a heterogeneous presentation that varies widely between patients. The challenge in detecting a significant difference lies in the fact that not all rodents (or humans for that matter) exposed to CO will go on to develop DNS. Nor will they all develop it at the same time. This is true even for individuals with the same exposure. The reasons for this are not well understood. We detected a trend that was beginning to manifest itself by days 6 and 8, but we had reached our end-point and our study design did not allow us to continue testing beyond this mark.

Both hydroxocobalamin and ascorbic acid are very safe, and none of our animals died after receiving the $B_{12r}$ solution. $B_{12r}$ has significant effects on oximeter readings which is why all samples containing $B_{12r}$ were analyzed with Resonance Raman and not standard oximetry. Hydroxocobalamin has been used safely for over 40 years in Europe and more recently in the US in patients with cyanide poisoning and smoke inhalation injury.

Summary Our data show that the novel synergism of hydroxocobalamin with ascorbic acid extracted CO through conversion to $CO_2$, independently of high-flow or high-pressure $O_2$. This resulted in a clinically-significant off-gassing of $CO_2$ at levels 5 to 8 times greater than controls, a clinically-significant reduction in COHgb half-life, and evidence of increased brain oxygenation and amelioration of microglial damage in rat models. Reduced hydroxocobalamin thus serves as an injectable antidote for CO toxicity.

References

1. Mowry, J. B., Spyker, D. A., Cantilena, L. R., Bailey, J. E. & Ford, M. 2012 Annual Report of the American Association of Poison Control Centers' National Poison Data System (NPDS): 30th Annual Report. Clin. Toxicol. Phila. Pa. 51, 949-1229 (2013).
2. Bhatia, R., Chacko, F., Lal, V. & Mittal, B. R. Reversible delayed neuropsychiatric syndrome following acute carbon monoxide exposure. Indian J. Occup. Environ. Med. 11, 80-82 (2007).
3. Buckley, N. A., Juurlink, D. N., Isbister, G., Bennett, M. H. & Lavonas, E. J. Hyperbaric oxygen for carbon monoxide poisoning. Cochrane Database Syst. Rev. Online CD002041 (2011).
4. Buckley, N. A. & Juurlink, D. N. Carbon monoxide treatment guidelines must acknowledge the limitations of the existing evidence. Am. J. Respir. Crit. Care Med. 187, 1390 (2013).
5. Schrauzer, G. N. & Lee, L. P. The reduction of vitamin B12a by carbon monoxide. Arch. Biochem. Biophys. 138, 16-25 (1970).
6. Roderique, J., author. Studies on the reaction of high-dose hydroxocobalamin and ascorbic acid with carbon monoxide: implications for treatment of carbon monoxide poisoning. (2013).
7. Brown, H. & Prescott, R. in Applied Mixed Models in Medicine 435-439 John Wiley & Sons, Ltd, (2006).
8. Nortje, J. & Gupta, A. K. The role of tissue oxygen monitoring in patients with acute brain injury. Br. J. Anaesth. 97, 95-106 (2006).
9. D'Hooge, R. & De Deyn, P. P. Applications of the Morris water maze in the study of learning and memory. Brain Res. Brain Res. Rev. 36, 60-90 (2001).
10. Vorhees, C. V. & Williams, M. T. Morris water maze: procedures for assessing spatial and related forms of learning and memory. Nat. Protoc. 1, 848-858 (2006).
11. Yang, A., Liu, N. & Kuznetsova, O. Modeling the treatment effect on a median of a percent change from baseline in a lognormal variable using SAS PROC NLMIXED. Paper SP01. (2009).
12. Hutson, C. B. et al. Traumatic brain injury in adult rats causes progressive nigrostriatal dopaminergic cell loss and enhanced vulnerability to the pesticide paraquat. J. Neurotrauma 28, 1783-1801 (2011).
13. Mikirova, N., Casciari, J., Rogers, A. & Taylor, P. Effect of high-dose intravenous vitamin C on inflammation in cancer patients. J. Transl. Med. 10, 189 (2012).
14. Uhl, W., Nolting, A., Golor, G., Rost, K. L. & Kovar, A. Safety of hydroxocobalamin in healthy volunteers in a randomized, placebo-controlled study. Clin. Toxicol. Phila. Pa. 44 Suppi 1, 17-28 (2006).

Example 2

Synthesis of Cobinamide

Several methods of synthesizing cobinamide exist. This Example describes the following methods:

Method 1: Generation of Cobinamide from Cyano-cobalamin via O-Acetyl-Cobinamide Intermediate.

Step 1. Generation of O-Acetyl-Cobinamide 100 mg cyano-cobalamin is dissolved at 0° to −2° C. in 5 ml of anhydrous hydrofluoric acid from 0 to −2° C. and offset dropwise with 0.3 ml of acetic anhydride. After 15 min the solvent is distilled off in a vacuum and the residue is subjected to phenol extraction. The crude product thus obtained is purified by cellulose column chromatography using water-saturated secButanol +0.01% HCN as mobile phase. Here, the main zone of the O-acetyl Cobinamide is separated from small amounts of byproducts. After another phenol extraction, the product is obtained in pure form. Yield: 91 percent.

Step 2: Conversion of O-Acetyl-Cobinamide to Cyano-Cobinamide 10 mg O-acetyl-cobinamide are dissolved in 10 ml of 1-molar aqueous solution of Piperidine at 0 to $-2°$ C. and allowed to stand at this temperature for 2 hrs. The mixture is washed three times with 4 mL of isopropyl ether/n-butanol (2:1) and the pH value is brought to 5.5 with diluted hydrochloric acid. The crude product is purified by phenol extraction on chromatography paper (Whatman 3 MM) with water-saturated sec Butanol +0.01% HCN. The main zone includes cyano cobinamide which is obtained in pure form following further extraction with phenol. Yield: 82 percent.

Step 3: Conversion of Dicyano-cobinamide to Diaquo-Cobinamide

Dicyano-cobinamide (30 mg) is dissolved in water (40 cm$^3$), and HClO$_4$(1 mol dm$^{-3}$) added to give pH 2-3. This is placed into an annular glass container with an outer diameter of 8.5 cm, a width of 3 mm between the two walls, and a height of 10 cm, open at the top. The hollow center accommodates a 60-W tungsten lamp. The annular space contains approximately 40 cm3 of solution, which is stirred and flushed with a fine stream of nitrogen bubbles emanating from the ends of four plastic capillary tubes. The container and bulb are all placed in a water-bath held at 0° C. and the resultant solution is photolysed in the annular cell until the reaction is complete (typically about 5 hrs). The extent of reaction is monitored by withdrawing a small sample of solution, diluting to the necessary concentration in NaOH (0.1 mol dm$^{-3}$), and examining the spectrum in the region of the γ-band. At this pH any unphotolysed dicyano-cobinamide (pK=11 .O) 7c is present as the hydroxocyano-complex which has a sharp y-band at 362 nm (εmolar=2.3×10$^4$ dm$^{-3}$ mol$^{-1}$ cm$^{-1}$), whose presence can readily be detected in the presence of photolysed dhc, the spectrum of which (see FIG. 3) includes a broad shoulder at ca. 356 nm (with ε$_{362}$ ca. 1.7×10$^4$ dm$^3$ mol-1 cm-1). After photolysis is complete, the solution of diaquo-cobinamide is carefully neutralized with NaOH (0.1 mol dm$^{-3}$), degassed by evacuation with a water-pump for 30 min, and may then be stored without further treatment as a frozen solution at $-20°$ C. for at least two months and probably longer. The diaquo-cobinamide cannot be separated from the low concentration of electrolyte by extraction through either phenol-chloroform or benzyl alcohol, since this causes partial reduction; however, separation can be accomplished, by using an Amicon 52 ultra-filtration unit with a Diaflo UM 2 ultra-filter. Solid diaquo-cobinamide can then be prepared by freeze-drying.

Method 2: Preparation of Cobyric Acid

Two hundred milligrams of cyanocobalamin (dried 24 hours at 80° C. over P$_2$O$_5$) is dissolved in 20 ml of dry methanol with mechanical stirring and heating to 50-60° C. Anhydrous zinc chloride (20 g) is added and dissolved. The mixture is protected from moisture and heated under reflux for 1 hour in an oil bath of 170° C. After cooling to room temperature, the solution is diluted to 100 ml with a 0.1% solution of HCN (A 1% solution of HCN is easily prepared by passing a solution of 2.4 g of KCN in 8 ml of water through a column (12×3 cm) of Dowex 50 X8 in the H-form and eluting the HCN with water at a slow flow rate. The first 30 ml of the effluent is discarded, then 100 ml is collected), and the corrinoids are extracted with a mixture of phenol and chloroform (1:1, w/v). The phenol-chloroform solution is washed with water. An equal volume of chloroform and half of this volume of n-butanol are added. Then the corrinoids are extracted into water; about 20% of the corrinoids remain in the organic phase, which is discarded. The aqueous solution is evaporated to dryness in vacuo, dissolved in 0.2 N acetate buffer, pH 4.5, containing 0.1% of HCN, and poured on a column of carboxymethyl cellulose (18×1.5 cm) or CM-Sephadex C-25 in the Na-form, previously equilibrated with the same buffer. By elution with this acetate buffer, cobinamide separates from the slower moving cobyric acid/3-aminoisopropyl ester. This ester is acetylated immediately at 0 to $-2°$ C. by dropwise addition of 5 ml of acetic anhydride with shaking. After 1 hour, the solution is washed two times with 10 ml of chloroform to remove the excess of acetic anhydride. The corrinoid is then purified by phenol extraction.

The cobyric acid beta-acetylaminoisopropyl ester is dissolved in 30 ml of 1 M piperidine solution at 0 to $-2°$ C. and left at this temperature for 2 hours. The solution is then washed three times with 30-ml portions of isopropyl ether-n-butanol (2:1, v/v) and acidified to pH 5.5 with diluted HCl. After another phenol extraction, cobyric acid is separated from minor impurities by chromatography on a cellulose column with n-butanol-water-1% HCN (85:14:1) as solvent or by descending paper chromatography with sec-butanol-water-1% HCN (70:29:1). The R$_{cobinamide}$ value of cobyric acid in the latter solvent is 0.53. After another phenol extraction, pure cobyric acid is obtained in 11% yield.

Method 3: Degradation Via Cerous Hydroxide/Methanol:

To a magnetically stirred solution of 6.4 g of cerous nitrate, Ce(NO$_3$)$_3$.6H+O, in 70 ml of water, concentrated ammonia (3.5-4.0 ml) is added dropwise until all the cerous hydroxide is precipitated. (Some commercial cerous nitrate preparations give colloidal hydroxide solutions when ammonia is added. In this case a 10% NaOH solution is used for the preparation of cerous hydroxide). The hydroxide is centrifuged for 3 minutes at 2000 rpm, the supernatant is decanted, the precipitate is suspended in 100 ml of water containing 0.3 ml of concentrated ammonia and centrifuged as above. This washing is repeated four times. In a 1-liter three-necked round-bottomed flask fitted with stirrer and reflux condenser, 500 mg of crystalline vitamin B$_{12}$ (crystal water, 12%) is dissolved under stirring in 150 ml of water. Then the suspension of cerous hydroxide in 100 ml of water is added followed by 2 ml of a 1% solution of HCN. (It is essential to use the cerous hydroxide immediately after preparation. Aged hydroxide is less effective). The mixture is placed in a boiling water bath and heated under stirring for 50 minutes. Within the first 20 minutes, the pH is checked at least every 5 minutes and maintained between 8 and 9 with ammonia (an essential step for complete cleavage). After cooling, the mixture is centrifuged for 5 minutes at 2000-3000 rpm. The supernatant is decanted. The precipitate is washed 4-5 times with 100 ml of water containing 0.3 ml of concentrated ammonia. The combined supernatants are evaporated to dryness in vacuo in a rotating evaporator.

The residue is dissolved in 8 ml of water and poured on a column (5×10 cm) of CM-Sephadex C-25 in the H-form. (If the cerous hydroxide initially used has been freed enough from salt, carboxymethylcellulose or phosphocellulose columns (5×30 cm) may also be used. Otherwise these columns may be used only after a phenol extraction of the material). Unreacted cyanocobalamin is eluted with water. Cobinamide is eluted as a purple band with 0.8 to 1 liter of 0.1%

HCN and brought to dryness in vacuo (yield, 320 mg). Molar absorbency indices of cobinamide dicyanide in 0.1% KCN: $30.6 \times 10^6$ cm$^2$/mole at 366 nm and $10.42 \times 10^6$ cm$^2$/mole at 580 nm. The column is washed with 0.5 liter of water to remove HCN. The dicyanocobinamide is then converted to diaquocobinamide according to Step 3 Method 1 above.

Method 4: Enzymatic Generation of Cobinamide from Culture

Step 1: Creation of Crude Enzyme Extract

To a stab-culture of *Propionibacterium shermanii* (*P. shermanii*) in a test tube, grown for 5 days at 30° C. in Micro Assay Culture Agar and then stored at ~−4° C. until used, 3 ml of Micro Inoculum Broth is added, and after suspension of the bacteria in the liquid with a sterile platinum needle, the tube is incubated for 3-4 hours at 30° C., then the liquid is transferred to 10 ml of Micro Inoculum Broth, and the culture is grown for 12-15 hours. The further subcultures are made in the following medium using always a 10% inoculum: 55 g of dry cornsteep powder are suspended in 1 liter of warm tap water and brought to pH 7.0-7.2 with 50% NaOH. This suspension is kept at 100° C. (for instance, in the autoclave) for about 15 minutes. The hot suspension is filtered through a folded paper filter. TM The filtrate is sterilized for 10-15 minutes at 120° C. Prior to inoculation, 10 ml of phosphate, 10 ml of yeast extract, and 20 ml of glucose, and after inoculation 1 ml of magnesium chloride and 1 ml of cobalt sulfate are added per liter. The pH of the inoculated fermentation has to be 6.8-7.0. The pH is adjusted twice a day with sodium carbonate. Glucose (20 ml per liter of fermentation broth) is added twice the first day and once the following days. Usually cultures 2-3 days old give a good starting material for the preparation of crude extracts. The bacteria are harvested and washed once or twice with distilled water; 20-30 g of wet cells are obtained per liter of fermentation broth. The bacteria can be stored at −30° C. for at least 3 months Preparation of Crude Extract. Twenty-five grams of cells are broken at −30° C. in the X-press (AB Biox, Nacka, Sweden). The pressed bacteria are suspended in 25 ml of 20 mM Tris-HCl buffer, pH 7.5, containing 1 mM EDTA, and treated with a small amount of deoxyribonuclease (EC 3.1.4.5). This suspension is centrifuged at 4-2° C. for 20 minutes at 20,000 rpm. The supernatant solution is decanted and the precipitate eluted again with 25 ml of Tris-EDTA buffer. The combined supernatant solutions usually contain 25-40 mg of protein per milliliter (biuret)

Step 2: Cobinamide Phosphate from Crude Extract

To 0.5 ml of Tris buffer, add 0.025 ml of cobinamide, 0.125 ml of ATP, 60 mg of protein from freshly prepared crude *P. shermanii* extract, and 0.05 ml of magnesium chloride (total volume 2.5 ml). In order to get $^{32}$P-labeled cobinamide phosphate, ATP-γ-$^{32}$P may be added. Incubate for 5 hours at 37° C. After incubation the mixture is brought to pH 5.0 with 0.3-0.4 ml of 1 M acetic acid, mixed and heated for 5 minutes in a boiling water bath. Then it is cooled down and centrifuged (5 minutes, 10,000 rpm). The supernatant solution is decanted and the residue is resuspended in 2 ml of water and centrifuged again. The corrinoid coenzymes are isolated from the combined supernatants by phenol extraction. The aqueous salt-free solution obtained after this operation is brought to dryness. The residue is dissolved in 0.05 ml of water, stripped on paper, and separated by electrophoresis in 0.5 M acetic acid (pH 2.7) at 15 V/cm for 1.5 hours. The fastest moving yellow compound is 5′-deoxyadenosyl-cobinamide (DA-cobinamide), which migrates toward the cathode with an electrophoretic mobility of 6.1 (cm$^2$/V×sec×$10^5$). DA-cobinamide phosphate has 45% of the mobility of DA-cobinamide, and DA-GDP-cobinamide moves as a sharp band with 11% of the mobility of DA-cobinamide to the cathode. DA-cobinamide phosphate may be further purified by descending paper chromatography with sec-butanol-water-acetic acid (70:30:1). RDA-cobinamide of DA-cobinamide phosphate is 0.2; of DA-GDP-cobinamide, 0.06. The yield of DA-cobinamide phosphate is 0.01-0.02 micromole. Five milligrams of KCN are added after incubation, the pH is brought to 6-7 with 0.2 ml of 1 N acetic acid, and the mixture is heated in a boiling water bath for 8 minutes. After centrifugation (5 minutes, 10,000 rpm) the supernatant is decanted; the precipitate is resuspended in 2 ml of water and centrifuged again. The corrinoids are isolated from the supernatant solutions by phenol extraction and separation by descending paper chromatography on Schleicher and Schuell paper 2043a with sec-butanol-water-acetic acid-KCN (70:30:1:0.01). $R_{cobinamide}$ value of cobinamide phosphate is 0.20, of GDP-cobinamide, 0.06.

Additional methods and details of methods may be found, for example, in Roth et al., Annu. Rev. Microbiol 1996. 50:137-81, and Baldwin et al., J. Chem. Soc. Dalton Trans 1983, pp. 217-223.

Example 3

Additional Experimental Data

Figure 9:
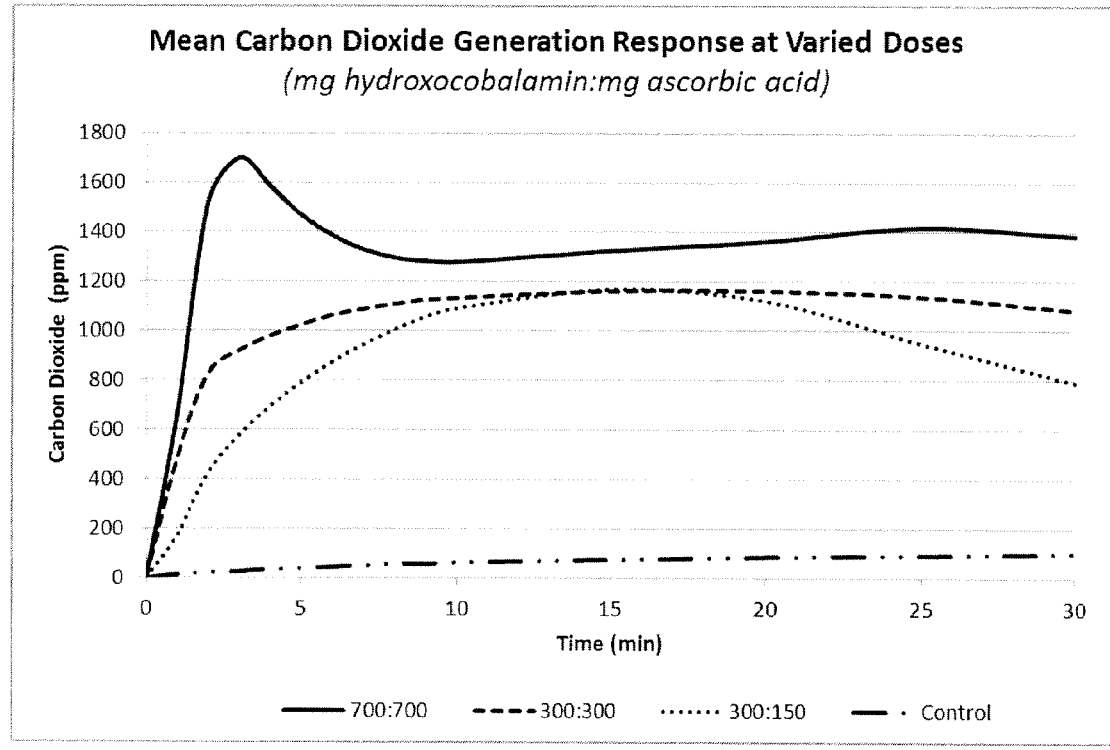
FIG. 9. $CO_2$ generation by dose.

FIG. 9 shows the results of $CO_2$ generation by dose experiments. The results demonstrate the changes in $CO_2$ generation with varying the concentration of (hydroxocobalamin:ascorbic acid). The control line is an aggregate of oxidized hydroxocobalamin in normal saline, and normal saline alone. The doses are in milligrams (i.e. milligrams of hydroxocobalamin: milligrams of ascorbic acid). Changing the concentration of ascorbic acid changes the concentration of reduced hydroxocobalamin in the mixture. Methods for FIG. 9: The antidote consists of a mixture of hydroxocobalamin HCl (OHCbl) and ascorbic acid in deoxygenated 0.9% NaCl solution (normal saline, NS). The addition of ascorbic acid to OHCbl was performed under anaerobic conditions in a glove box under nitrogen environment. To prevent red cell lysis, deoxygenated NS (0.9% NaCl in water, Baxter, Inc.) was used as the solvent. The NS was deoxygenated by placing it in a cleaned, sterilized flat-bottomed glass vacuum flask and placed under vacuum for 30 minutes, and then aerated with nitrogen gas while still under vacuum for an additional 60 minutes. Three concentrations were used during these experiments: 700 mg of OHCbl: 700 mg ascorbic acid, 300 mg of OHCbl: 300 mg ascorbic acid, and 300 mg OHCbl: 150 mg ascorbic acid. In each case these amounts were dissolved in 5 mL of deoxygenated NS. We created a closed-loop artificial circulation system using the Maquet Pediatric Quadrox-iD® hollow-fiber membrane oxygenators. For consistency, all tubing and supplies were also from MaquetGetinge Corp. Blood was circulated with a roller pump (Stöckert/Shiley®). Blood was maintained at 37° C. by countercurrent water flow heat exchanger (Thermo-Haake model DC 10®). With each experiment, 150 mL of blood was injected into the system until it was full, and there was no longer any air visible in any of the tubing or in the oxygenator. After priming the system with blood the roller-pump was set to a rate of 250 mL/minute which circulated approximately the entire blood volume about 1.5 times per minute. We incorporated fluid sampling ports with luer-lock adapters and three-way stopcocks into the circulation pathway to allow for blood sampling and antidote injection.

Aseptic technique was followed at all times. Gas from the gas-out port of the oxygenator was routed in parallel to two analyzers. The carrier gas for the experiments was compressed medical grade air (Airgas International). Carbon Dioxide ($CO_2$) concentration was captured by a $CO_2$100 c module from BIOPAC Corp. Carbon Monoxide (CO) concentration was captured by a Horiba VIA-510® model CO monitor. The CO and $CO_2$ monitors were set to a sampling rate of 10 samples/second. Gas analyzers were calibrated weekly to a resolution of 0.035% (span drift of 0.002%). Continuous gas monitoring data were amplified and acquired by an MP150® using AcqKnowledge 4.0 Software® (BIOPAC Inc.Galeta Calif.). CO and $CO_2$ concentrations were in ppm/minute, plotted over 30 minutes from the time of antidote injection. After baseline data were obtained, the in-flow gas mixture was switched to 6,000 ppm CO in research grade air (0.5838% v/v CO, balance air) for 20 minutes at a flow rate of 178 mL/min. A second 0.6 mL blood sample was taken and analyzed as before by both the standard blood gas analyzer and RR spectroscopy. If a value of 50% (+/-5%) carboxyhemoglobin (COHgb) was established then the in-flow gas mixture was returned to medical grade air at a flow rate of approximately 178 mL/min. If the COHgb level was too low, then the flow of CO was maintained at 5-10 minute intervals until the desired level was achieved. One liter of 99% $^{13}C$ labeled CO was obtained from Cambridge Isotope Laboratories. The same circulation system and protocol was used as for the antidote experiments, with the exception that the gas-in and gas-out lines were clamped to prevent $CO_2$ trapped in the blood from escaping. Following a rewarming period to normal physiologic temp of 37° C. a sample of 300 mL of gas was removed from the oxygenator by syringe and injected into a 300 mL breath-bag (Ostuka Pharmaceutical Co.). Twenty mL of pure CO was injected into the oxygenator and given 30 minutes to equilibrate with Hgb. A blood sample was drawn to ensure adequate COHgb concentration. The 300:300 concentration of the antidote solution (300 mg OHCbl with 300 mg ascorbic acid in 5 mL NS) was then injected. Following a twenty minute equilibration period, another 300 mL sample of gas was removed from the oxygenator and infused into a breath-bag. We detected $^{13}CO_2$ production by measuring the increase in the $^{13}CO_2/^{12}CO_2$ ratio in the "exhaled" post-antidote gas using an infrared spectral analyzer (POCone, Otsuka Pharmaceutical Co.). This analyzer determines the relative change in $^{13}CO_2/^{12}CO_2$ compared to the baseline sample with a resolution of 0.1 per mil (0/00). Using the same protocol a fresh oxygenator was setup and antidote was injected into blood that was not exposed to $^{13}CO$. Non-interference by the presence of $^{13}CO$ in the sample was verified by using a control gas containing 50,000 ppm $CO_2$ as the baseline, and comparing it with the same gas infused with $^{13}CO$.

Results/Conclusions: These data indicate that the mixture of OHCbl and ascorbic acid in blood containing COHgb is capable of converting CO to $CO_2$. This is an important finding with significant clinical implications since both of these compounds are safe and approved for use in humans even at high doses. Although both ascorbic acid and OHCbl are being used increasingly in the settings of trauma, burn, and smoke inhalation, this is the first study that suggests a novel set of capabilities when the two are combined at high dose. This study also indicates that these compounds may be effective whether they are given either together or separately but spaced closely in time. The potential to extract CO from the body, by conversion to $CO_2$, independently of high-flow or high-pressure $O_2$ is a novel finding.

Our results show that it is only the combination of OHCbl and ascorbic acid (rather than the presence of components in isolation) that results in a significant increase in $pCO_2$. We found no evidence to suggest that this was from a breakdown of either antidote or blood components. In order to verify that the $CO_2$ being generated was due to conversion of CO to $CO_2$ by the antidote we used $^{13}C$ labeled CO and then detected the change in the $^{13}CO_2/^{12}CO_2$ ratio using an infrared spectral analyzer. The baseline sample was taken after exposing the blood to $^{13}CO$. Antidote was injected into the blood, given 20 minutes to equilibrate and then the second sample was taken. We detected a 16.7% increase in the $^{13}CO_2/^{12}CO_2$ ratio over baseline. Infusing a standard sample with $^{13}CO$ caused no interference in the analysis of $^{13}CO_2$. The increase in the $^{13}CO_2/^{12}CO_2$ ratio after poisoning with $^{13}CO$ clearly indicated that the $CO_2$ being generated was from the conversion of CO to $CO_2$.

Figure 10:
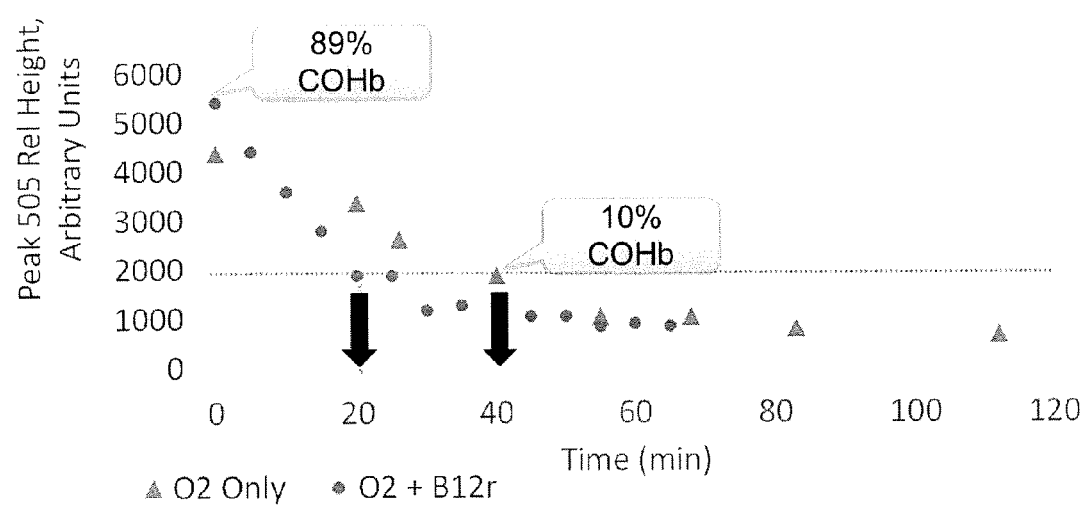
FIG. 10. Half-life reduction.

FIG. 10 shows the results of half-life reduction experiments. The results show the reduction in the half-life of carboxyhemoglobin to 19 minutes after adding reduced hydroxocobalamin compared with simply exposing the blood to high-flow oxygen.

Figure 11:
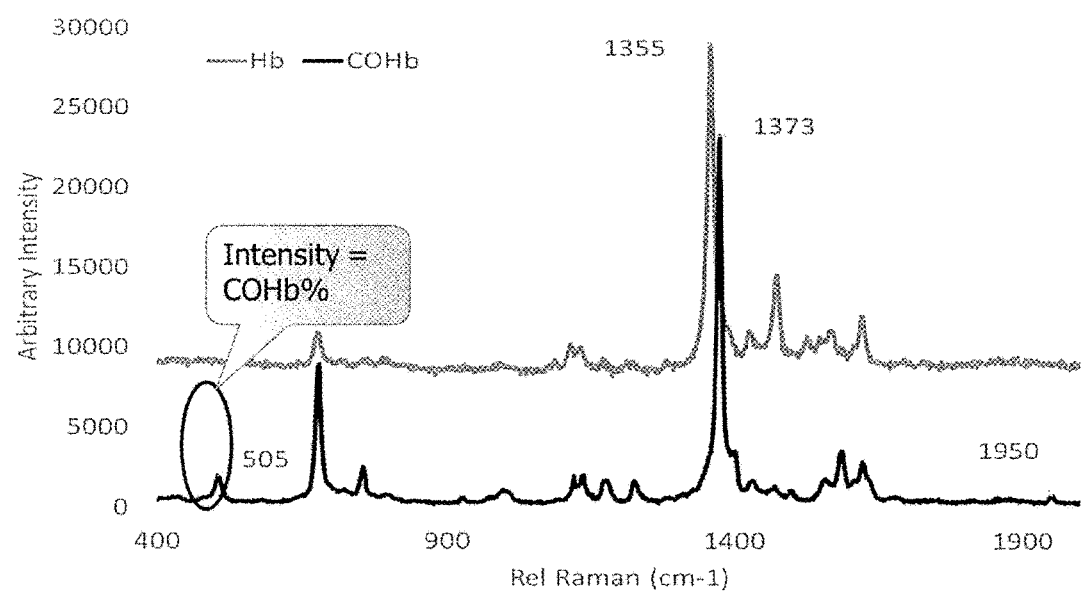
FIG. 11. Measurement of the concentration of carboxyhemoglobin in the blood using Resonance Raman spectroscopy.

Results presented in FIG. 11 show that Resonance Raman spectroscopy can isolate the spectra of carboxyhemoglobin and allows the use of the height of the 505 peak (circled) to calculate the concentration of carboxyhemoglobin in the blood.

Methods for FIGS. 10 and 11: Human blood was obtained from anonymous donors via the VCU Health System Apheresis Clinic's phlebotomy program. Blood obtained for research was restricted to non-sickle cell and non-HIV donors. The blood was treated with 1000 units of Heparin per 100 ml of blood in sterile blood donation bags, stored in the laboratory refrigerator and used within 5 days of the phlebotomy. Stored blood bags were turned over to unsettle blood daily and prior to use. Prior to experiments, blood bags were brought to room temperature and filtered using transfusion lines with clot filters as a precaution against blood clots; little to no clotting was observed, and blood with significant clotting activity were discarded. Blood would be circulated in the gas-exchange system to obtain target COHb percent concentration levels (apparatus described below). Blood samples were obtained from the experiment apparatus, and analyzed with one of two blood gas machines available. The Radiometer™ ABL 800 clinical blood gas analyzer and the Radiometer™ OSM3 research blood gas analyzer. The ABL 800 is capable of measure $pO_2$, $pCO_2$, % $HbO_2$, % HbCO, % MetHb, pH, and $O_2$ Content. The OSM3 is only capable of measuring % $HbO_2$, % HbCO, % MetHb and $O_2$ Content.

Preparation of Reduced Hydroxocobalamin

Hydroxocobalamin (OHCbl), or Vitamin B12, in powder form and pharmaceutical grade buffered L-Ascorbic Acid (AA) were obtained from Sigma-Aldrich. Both were stored refrigerated and sealed away from light in brown bottles (from manufacturer) or in clear vials wrapped in foil as needed. The AA was also maintained in an $O_2$ free environment, and diluted with normal saline. The normal saline used was degassed with several cycles of vacuum and $N_2$ gas exposure, then stored in laboratory glass containers filled with $N_2$. All mention of normal saline in this study will refer to this degassed saline source unless otherwise noted.

Preparation of the antidote was executed in a room temperature, positive pressure, $N_2$ glove box by mixing B12 with the AA in syringes, and taking the solution out of the glove box in the stoppered syringe with needle. Great care was conducted to ensure preparation and handling in an $O_2$-devoid environment prior to use. Target concentrations for most uses ranged from 1 mg of B12 per ml of blood to 10 mg/ml B12r/blood. Concentrations are indicated in the individual results discussed.

Raman Spectroscopy System

The Raman setup included: a 406.7 nm krypton laser excitation source (Coherent Saber), various optics to optimize the excitation beam onto the sample flowing through a capillary tube, more optics to collect the emission light, a spectrometer fitted with a 600 mm grating, and a CCD camera (Princeton Instruments Python CCD) connected to a computer running spectroscopy recording software (Princeton Instrument WinSpec32). The excitation laser beam hits the flowing blood through the capillary tube orthogonal to the emission light being collected. The system was mounted on a laboratory table along with the blood circulating systems described below. Laser output power was 0.7 mW to 08 mW, but was attenuated by a neutral density filter to 0.07 mW or 0.08 mW prior to hitting the sample. Collection of spectra was 3 to 5 minutes in 20 s exposure frames summed together by the software program. The low power was necessary to ensure very minimal effect of photolysis of CO and $O_2$ from Hemoglobin.

Gas Exchange Systems

Raman measurements were taken via three methods: blood circulating in a non-gas exchange setup or in a gas exchange setup (both described below), or via capillary tubes of non-flowing fluids. The experiments occurred at room temperature and noted to be between 22 and 24 degrees Celsius. A primary purpose to using a circulating system for blood was to further minimize photolysis of the gases bound to hemoglobin, and the other is to ensure thorough mixing of the B12r with blood.

The non-gas exchange system used a peristaltic pump to facilitate the flow of blood through TYGON™ tubing and a capillary tube. A syringe was used to allow volume changes to prevent pressure changes in the system. The internal volume of the setup was 5 ml. The syringe allowed for up to 8 ml; however, minimal fluid was used to prevent areas of stagnant blood. This non-gas exchange system was used because we were interested in observing anaerobic B12r effects on Hb with the trapped gases in blood, and with no extra variable of gas-exchange. The gas exchange setup used a MAQUET™ QUADROX-ID Pediatric Oxygenator with TYGON™ tubing. A shunt was made to divert a portion of the blood flow through smaller TYGON™ tubing and a capillary tube. The Gas Out port was attached to tubing, the end of which was placed into a lab hood. The Gas In port was used to introduce various gases. Tanks of 100% 0, or 100% $N_2$ were used to flow through the gas ports. Air-tight syringes were used to inject 100% CO, carefully, into the system. The gas ports were either left open to allow flow, or clamped to trap the gases in the MAQUET™ unit as needed. The circulating fluid volume of the system was 135 ml.

The blood was sampled periodically for COHb and $O_2$ Saturation or $HbO_2$ concentration depending on the gas analyzer used, and immediately sampled for Raman spectra within 5 minutes.

For the reduction of B12r, various AA:B12a mass ratios were explored from 1:1 down to 0.08:1. Molar calculations showed that to completely reduce B12a to B12r, a 0.08:1 mass ratio was sufficient; however, analysis with Raman spectroscopy showed significant signals for B12a and weak B12r signals in the 0.08:1 solution produced (FIG. 11, second spectrum from top). The 1:1 mixture showed a Raman spectra with strong B12r signals and undetectable B12a signals from the raw spectrum.

Results/Conclusions: COHgb half-life $t_{1/2}$ was 33 (95% CI 27, 42) min under $O_2$ alone, but was reduced to 18 (95% CI 15, 21) min with $B_{12r}$ infusion, a difference of 15 min (p<0.001). This reduction in COHgb half-life demonstrates that addition of reduced hydroxocobalamin allows for significantly faster clearance of CO from the blood of affected individuals and provides further evidence to suggest a clinically relevant benefit to its administration. These results demonstrate that Resonance Raman spectroscopy is capable of detecting the presence of carboxyhemoglobin as distinct from other species of hemoglobin and as distinct from hydroxocobalamin. Absorption would be in line with the Beer-Lambert law, that absorption of specific energies of light has a predictable absorption profile in a chemical medium, and this absorption is directly proportional to concentration. Since the 505 $cm^{-1}$ peak of carboxyhemoglobin is the 415 nm wavelength and the 1950 cm peak is the 441 nm wavelength, absorption profiles for B12r and the excitation laser can be used in a mathematical model to measure B12r concentration.

Figure 12:
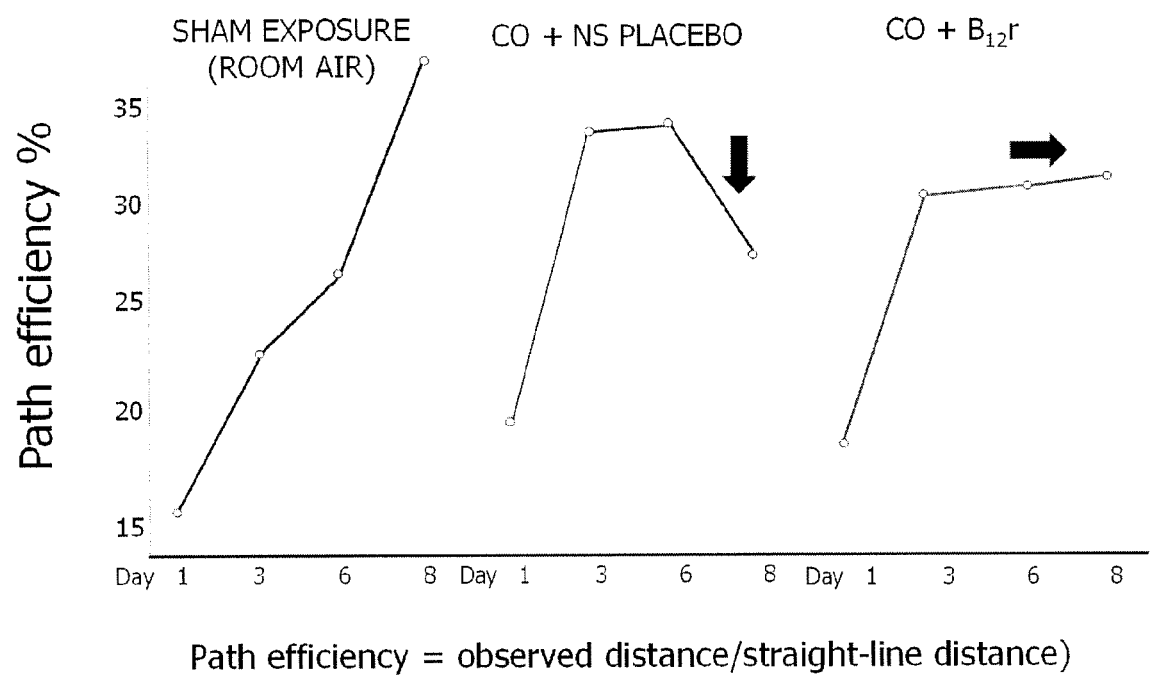
FIG. 12. Effect of administration of reduced hydroxocobalamin on efficiency of rats finding platform submerged under water from memory after CO exposure.

FIG. 12 is a path efficiency figure showing that injection of reduced hydroxocobalamin into rats following exposure to carbon monoxide resulted in improvement in their ability to memorize and swim accurately to the hidden submerged platform. As can be seen, exposure to reduced hydroxocobalamin significantly improved the cognitive ability of CO-exposed rats.

Methods for FIG. 12: All procedures followed the guidelines established in the Guide for the Care and Use of Laboratory Animals (U.S. Department of Health and Human Services) and were approved by the Institutional Animal Care and Use Committee of Virginia Commonwealth University (Protocol Number AD10000569). Long Evans Rats (LE rats) were used in the neurological testing. LE Rats were used in the Morris Water Maze test. These were obtained from Harlan Laboratories, Inc, and weighed 211±6 grams (LE Rats). All rats were housed two in each cage, and maintained by VCU Department of Animal Resources veterinarian staff in environments approved for rats. Rats were acclimated and their weights were monitored for a minimum 5 days prior to insult with CO or insult with Medical Grade Air (Air) as the control. During acclimation, rats were habituated to handling by experimenters. After insult animal weights were monitored for at least 3 days, and on each day of neurological behavior testing. After behavior testing, rats were euthanized with an intra-peritoneal injection of Sodium Barbital and monitored until the animals' heart beats were no longer detectable. Some rats from each treatment group were randomly selected for perfusion and brain harvesting for brain histology comparisons for a separate study.

Rats were divided into Control, Exposed Treated, and Exposed Untreated groups upon arrival. Morris Water Maze rats were ordered, underwent insult, and tested in blocks of 12. Modeled after various published CO injury protocols, rats were exposed to either CO or Air in 2 L air-tight chambers with the gases flowing at 0.5 L/min after an initial two minutes at 2 L/min. For the CO exposure, rats were exposed to CO at 2500 ppm for 60 min, and then at 6000 ppm for a maximum 10 min or until the animal was no longer responsive to stimuli. To keep mortality low, CO flow was interrupted for a few minutes with Air as needed near the 60-minute point prior to the 6000 ppm exposure phase, but total exposure time was maintained at 60 minutes. After insult rats were administered treatment per their group assignment. With the exception of $O_2$ treatment was given via intra-peritoneal injection. $O_2$ treatment was administered in a 7 L induction chamber with 100% $O_2$ flowing at 1

L/min; the chamber was already primed with 0, prior to inserting the animal. Rats were placed in a separate holding cage until they regained normal response to stimuli, and then placed into their primary housing cage thereafter.

Morris Water Maze Behavioral Tests

In the Morris Water Maze (MWM) test, a platform is submerged in a 1.8 m diameter pool filled with water to approximately 0.5 m such that an escape platform was submerged 2-2.5 cm below the surface of the water. The water was made opaque with white paint so that the platform was not visible, and the temperature was maintained between 25-27 degrees Celsius with a heat exchange pump. The pump was removed during the swim trials. The location of the platform was changed between Stages of the MWM test as follows: Day 1 in the NE Quadrant, Day 2 in the NW Quadrant, Day 3 in the SE Quadrant, and Day 4 in the center of the pool. A Stage of the MWM was conducted in a day. Within each Stage there were four swim trials for the rat to perform. For each trial the start position of the swim was change between North, South, East and West starting points. Within each Stage, the start order was constant between Trials, and randomized between Stages. The pool room has visual cues on the walls and other visual features that remained unchanged during the entire MWM experiments for consistent cues. The rat is placed gently, keeping their heads from submerging, at the start position facing the wall; and the software tracking begins. The AnyMaze™ system tracks the rat via a camera centered about 10 feet above the pool. AnyMaze marks the end of the trial at 60 seconds or when the rat has successfully climbed onto the escape platform, whichever comes first. The software recorded path efficiency for later analysis. After each swim trial, the rat is placed into a holding cage under a heat lamp with towels for 10 minutes prior to the next swim trial. LE Rats underwent MWM tests on Days 1, 3, 6 and 8 post-exposure; these days correspond to Stages 1 to 4 respectively. The animal handler, separate from the author, was blinded to the treatment group assignments.

Results/Conclusions: There were no statistical differences between treatments at any time point ($p > 0.2$) although weak differences in learning trajectories were suggested by examination of medians. Rats exposed to medical air only showed the expected daily increase in path efficiency; efficiencies increased by an average of 8-10% per day over eight days of testing. In contrast, both CO-exposed groups showed a plateau in performance with either no change (Co-B12r) or a modest decline (CONS 7%). Overall this is suggestive of a neuro-protective effect provided by rapid injection of reduced hydroxocobalamin when given immediately following exposure to carbon monoxide since it prevented the decline in performance seen in the exposed rats who only received placebo (normal saline).

Figure 13:
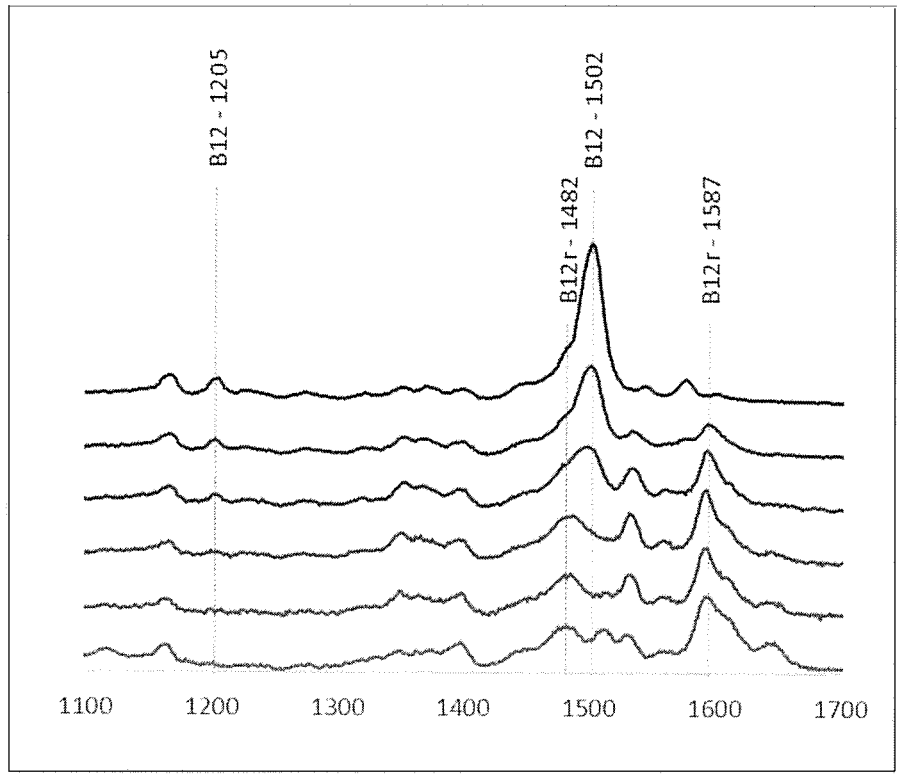
FIG. 13. UV-Vis Spectra demonstrating successful generation of reduced hydroxocobalamin using ascorbic acid. Oxidized hydroxocobalamin (B12a) "dotted" line. Reduced hydroxocobalamin following addition of ascorbic acid (B12r) "dashed" line. Regeneration of oxidized hydroxocobalamin following exposure to air "dotted-dashed" line.

FIG. 13 shows the conversion of B12 to B12r in "real-time" with varying concentrations of ascorbic acid, as measured by Raman spectroscopy. As can be seen, as increasing amounts of ascorbic acid are added to B12 (keeping B12 concentration constant), the B12 Raman Signal (top) decreases in intensity and B12r Raman Signal (bottom) is more pronounced. This shows that reduced hydroxocobalamin can be created by the addition of ascorbic acid to a solution containing oxidized hydroxocobalamin.

Figure 14:
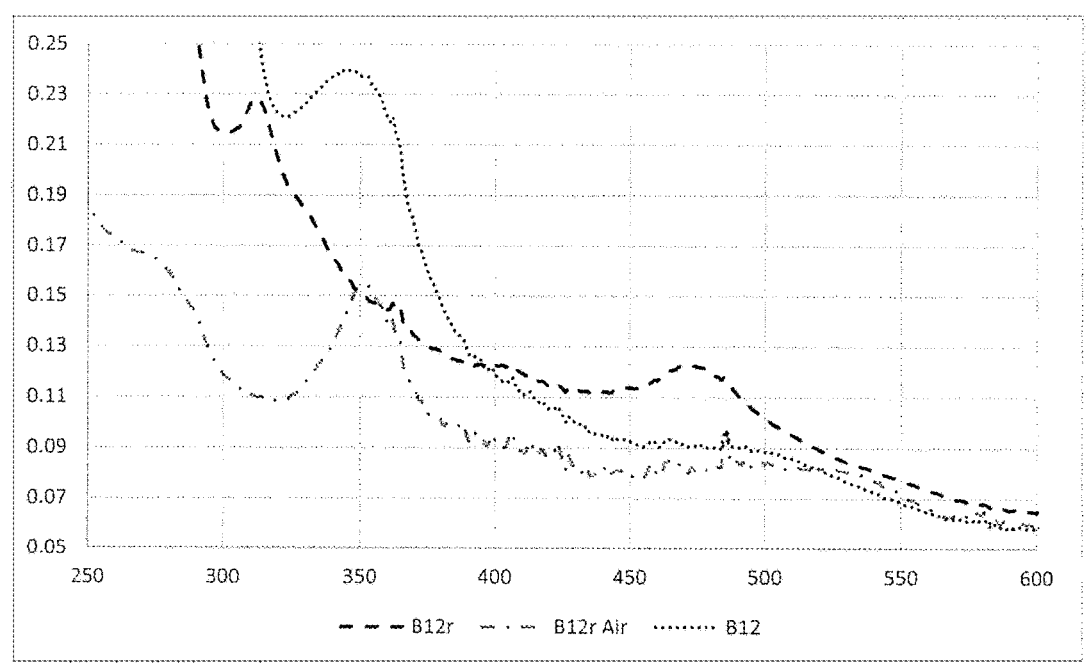
FIG. 14. Raman spectrum of B12:B12r mixtures with Rel Raman ($cm^{-1}$) on the horizontal and arbitrary intensity on the vertical axis. Prominent peaks that identify each chemical have been labeled.

FIG. 14 shows UV-Vis data demonstrating that reduced hydroxocobalamin can be created by the addition of ascorbic acid to a solution containing oxidized hydroxocobalamin, and that the reaction is reversible by exposing the reduced hydroxocobalamin to air. A standard solution of hydroxocobalamin in purified de-ionized water (1 mg/mL) was created at room temperature and standard atmospheric pressure in an oxygen free, nitrogen environment this solution was serially diluted in standard fashion and sealed in gas impermeable cuvets with a rubber top to allow injection of materials. Following spectral analysis, a 1 mg/mL solution of ascorbic acid was injected into the cuvet to give a 1:1 molar ratio of ascorbic acid to hydroxocobalamin and the spectrum was again taken. Following this, the top of the cuvet was removed and the solution was allowed to stand under room air. After 30 minutes a final spectrum was taken demonstrating the effect of oxygen on the reduced hydroxocobalamin solution.

Results/Conclusions: The results of these analyses show that reduced hydroxocobalamin can be easily formed from oxidized hydroxocobalamin with addition of ascorbic acid when performed under anaerobic conditions. In addition, these results demonstrate that the reaction is reversible and re-oxidation occurs quickly once reduced hydroxocobalamin is exposed to air.

While the invention has been described in terms of its several exemplary embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

I claim:

1. A pharmaceutical composition,
   consisting of
     hydroxocobalamin and/or cobinamide in a reduced form,
     at least one reducing agent, and
     a pharmaceutically acceptable carrier,
   wherein said pharmaceutical composition is de-oxygenated by producing and maintaining the pharmaceutical composition in an oxygen free environment.

2. The pharmaceutical composition of claim 1, wherein a concentration of the hydroxocobalamin and/or cobinamide is from about 5 mg/ml to about 25 mg/ml and wherein a mass ratio of the at least one reducing agent to the hydroxocobalamin and/or cobinamide is from 0.2:1 to 1:1.

3. The pharmaceutical composition of claim 1, wherein said reducing agent is ascorbic acid.

4. The pharmaceutical composition of claim 1, wherein an oxidation state of at least a portion of cobalt in said hydroxocobalamin and/or said cobinamide is 2+.

5. A medicament consisting of
   a reduced Vitamin B12 compound in an inert environment suitable for delivery to a subject, said reduced Vitamin B12 compound being selected from the group consisting of reduced hydroxocobalamin and reduced cobinamide;
   one or more reducing agents; and
   pharmaceutically acceptable salts;
   wherein said medicament is de-oxygenated by producing and maintaining the medicament in an oxygen-free environment.

6. The medicament of claim 5, wherein a concentration of the reduced Vitamin B12 compound is from about 5 mg/ml to about 25 mg/ml and wherein a mass ratio of the one or more reducing agents to the reduced Vitamin B12 compound is from 0.2:1 to 1:1.

7. The medicament of claim 5, wherein said one or more reducing agents are selected from the group consisting of ascorbic acid, zinc-mercury amalgam, Lindlar catalyst, sodium borohydride, sodium dithionate, formic acid, and platinum oxide.

8. The medicament of claim 5, wherein said inert environment comprises one or more inert gases.

9. The medicament of claim 5, wherein said inert environment comprises a deoxygenated liquid.

\* \* \* \* \*